US010610457B1

(12) United States Patent
Patel et al.

(10) Patent No.: US 10,610,457 B1
(45) Date of Patent: Apr. 7, 2020

(54) SYSTEM AND METHOD FOR STORING MEDICATION AND ALERTING USERS AND CAREGIVERS FOR TIMELY INTAKE

(71) Applicants: Miteshkumar Ishwarbhai Patel, San Leandro, CA (US); Raj Kalpesh Patel, San Jose, CA (US)

(72) Inventors: Miteshkumar Ishwarbhai Patel, San Leandro, CA (US); Raj Kalpesh Patel, San Jose, CA (US)

( * ) Notice: Subject to any disclaimer, the term of this patent is extended or adjusted under 35 U.S.C. 154(b) by 0 days.

(21) Appl. No.: 16/132,410

(22) Filed: Sep. 15, 2018

(51) Int. Cl.
*A61J 7/04* (2006.01)
*G16H 20/10* (2018.01)
(Continued)

(52) U.S. Cl.
CPC ........... *A61J 7/0436* (2015.05); *A61J 7/0418* (2015.05); *A61J 7/0481* (2013.01);
(Continued)

(58) Field of Classification Search
CPC combination set(s) only.
See application file for complete search history.

(56) References Cited

U.S. PATENT DOCUMENTS

| 2009/0315702 A1* | 12/2009 | Cohen Alloro | G06F 19/3462 340/539.1 |
| 2016/0000657 A1* | 1/2016 | Dickie | A61J 7/0481 206/534 |
| 2016/0074283 A1* | 3/2016 | Aggarwal | A61J 7/04 206/534 |

* cited by examiner

*Primary Examiner* — Travis R Hunnings

(74) *Attorney, Agent, or Firm* — Creso Legal; Firasat Ali

(57) ABSTRACT

A computerized pill intake reminder device is disclosed. The computerized pill intake reminder device is used for storing pills, detecting the number of pills in each pouch of the blister pack, inventory management, reminding users to take their medication on time, alerting by providing an audible or a visual alarm if the medications are not taken on time and as a secondary mechanism alerting their caregiver if the user has not responded to the alert and taken the medication on time.

The device includes a top housing and a bottom housing that can be rotated about each other to form a closed and sealed module. It also includes a processor that is communicatively coupled through an electronic circuit to a plurality of electronic components housed within the pill intake reminder device. These include a speaker, microphone, infrared sensors, cameras, LED lights, microphone, RFID scanner, non-volatile memory, transmitter, and a receiver. The LED lights can be programmed with various colors.

The speaker is used to sound an audible alarm play an audible message at a specific time to remind the user to take their medication or provide an alert if the time has passed. The device also includes a pill storage module that has an upper and a lower packing plate. The space in between the plates is where the blister pack is inserted.

The device includes a pill detection module. This module includes an infrared sensor (IR) and a camera. In operation, the processor causes the infrared sensor to detect the presence of a pill inside the pouch of the pill/blister pack and the processor causes the camera to quantify the number of pills in the pouch. The pill detection is performed by using a combination of IR Sensors, photodiodes, and a light emitting mechanism. A light beam, or an array of light beams, are passed from one side of the pouch to another and the light that passes through is read by the IR sensors and used for determining whether the pouch includes pills.

The device includes a guidance system to guide the user of the pill intake reminder device to a specific pouch of the pill/blister pack for retrieving pills stored in that pouch. It does so by illuminating a light emitting diode (LED) on or (Continued)

around a specific pouch from which medication/pills are to be retrieved by the user. It operates by obtaining the hours of administration (HOA) schedule for the patient and then locating a pouch of the pill/blister pack that correlates with the HOA schedule. Once located, the pouch is illuminated for guidance.

The device includes a display that can be used for providing visual alerts, videos, or recorded messages for instructing the user for taking the pills.

The device uses a transmitter to send alerts to mobile phone for reminding the user to take the medication as well as sending an alert for missing or noncompliance.

The radio frequency identification (RFID) reader is used to verify that a correct pill/blister pack, the one that is associated with the user/patient is being inserted into the device. The verifying process includes scanning an RFID tag located on the blister pack and matching it to patient information.

The device also performs periodic inventory of the pills in the blister pack. This includes using an infrared sensor housed within the electronic module to determine the presence of one or more pills in the pouch and using a camera housed underneath the pouch to image and count the number of pills that are in the pouch. The inventory serves as an error check to ensure that the right number of pills from the right pouch were taken by the user at their HOA. The pill inventory system also is used to re-order more medication, if allowed by the prescription, when it detects that it is time to replenish them.

19 Claims, 14 Drawing Sheets

(51) Int. Cl.
*G06K 7/10* (2006.01)
*G08B 21/24* (2006.01)
*G07C 9/37* (2020.01)
*A61J 1/03* (2006.01)

(52) U.S. Cl.
CPC .......... *G06K 7/10297* (2013.01); *G07C 9/37* (2020.01); *G08B 21/24* (2013.01); *G16H 20/10* (2018.01); *A61J 1/03* (2013.01); *A61J 2200/30* (2013.01); *A61J 2200/70* (2013.01); *A61J 2205/60* (2013.01); *A61J 2205/70* (2013.01)

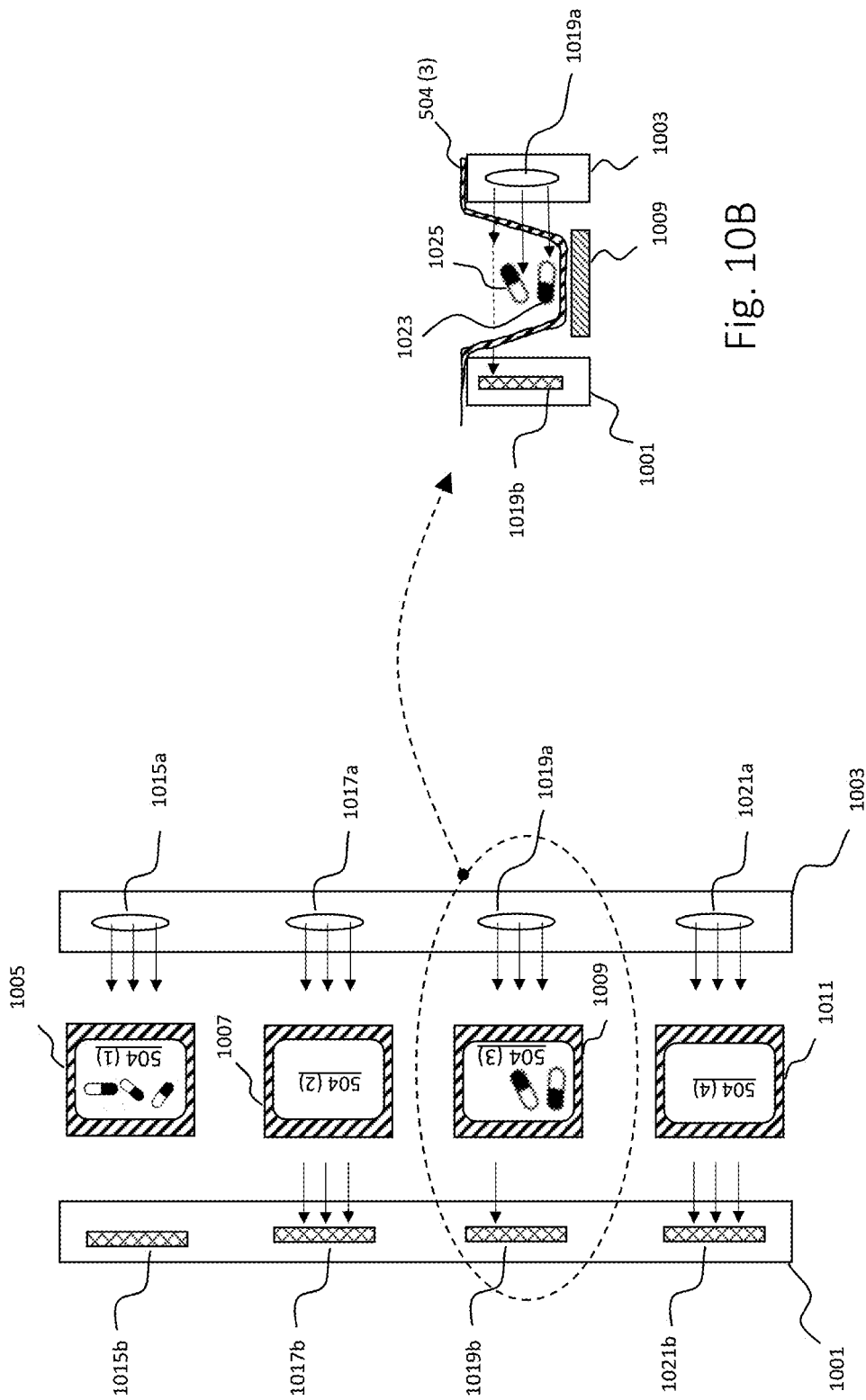

SYSTEM AND METHOD FOR STORING MEDICATION AND ALERTING USERS AND CAREGIVERS FOR TIMELY INTAKE

FIELD OF THE INVENTION

The present invention relates generally to pill containers and electronic reminders and management associated with such containers for taking medication on time. More specifically, the present invention relates to a laptop-like container that includes on-board electronic devices, processor, and memory for electronically reminding and managing pill storage and intake by a user.

DISCUSSION OF THE RELATED ART

It is common for patients to forget to take their daily dosages of pills. With life being busy and requiring our attention on numerous tasks, it is easy to forget to take a certain prescribed medication or a grouping of pills. At times a patient may remember to take the pill but still not take it at the right time or delay it as other things get in the way.

As medicine gets advanced and more solutions are discovered to address health issues in patients, doctors are having to prescribe a higher number of pills, including some pills that are critical to be taken at a particular time or within a certain window of time, and pills that are high in dosage and powerful, to help the patient regulate their health or cure a certain ailment.

Several studies show that there are lower levels of compliance by the patient when a higher number of pills are prescribed and required to be taken on a daily basis. It's also been reported that 40% of prescriptions fail to produce desired results because of noncompliance, improper regimen intake, or improper use.

There are several reasons for such noncompliance. These include forgetfulness, misplacing the pills, taking the wrong pills, or a patient not fully understanding the proper intake instructions. Patients may also get tired and disinterested in taking multiple pills and tend to ignore taking it unless reminded or pushed to do so. If the patient is of old age, or suffering from amnesia or dementia, it further adds to the confusion as they may not understand or be alert to take the medication at the right time.

Aside from causing further health problems and not curing the ailments, the non-compliance in many cases can be very detrimental to a patient's health and even life threatening. In certain cases, where a variety of drugs are involved, or when the patient has drug related issues, noncompliance may also cause the patient to undergo adverse drug reactions. Other issues caused by non-compliance include additional costs to the health care system in continuing to treat the patient.

Several attempts have been made to remind the patients to take their medications on time. A few such attempts are described below. It is noted that although some attempts by others are described here, we do not admit that any of them qualify as prior art to our invention.

One set of such attempts include a type of pill container or pill vial that has a reminder setting. Such attempts include a circular cap having the days of the week listed on top. The user is able to rotate the cap to a day of the week that corresponds with the current day and then able to remove only those pills that were deposited in the chamber inside the vial that is destined for that day. For example, on a Thursday, the user may rotate the cap to Thursday, as oppose to Tuesday or Wednesday, and since the vial would have a cavity for each day of the week that is separated from the other days of the week, the user would be able to take out only pills for Thursday. This solution still requires due diligence on the part of the patient and does not solve the non-compliance problem. The patient may even forget where they kept the pill container or in certain cases, such as old age or dementia patients, may be either unable to properly operate or understand the workings of the pill container.

Yet another attempt is made through alarm clocks and box like containers with different days of the week. The issue of non-compliance, forgetfulness still remains and are not solved by these systems.

Another problem is that elders purposely cheat the system and not take the pills as they may be fed up with the continuous intake of pills or just lost the desire to take the pills unless forced to do so, or reminded to do so—and the above systems do not provide a strong reminding or accountability mechanism to ease their taking of medication in proper dosage and on time. As such a system that provides a reminding and mechanism to cure the above-mentioned drawbacks is needed.

SUMMARY OF THE INVENTION

A computerized pill intake reminder device is disclosed. The computerized pill intake reminder device is used for storing pills, detecting the number of pills in each pouch of the blister pack, reminding users to take their medication on time, alerting by providing an audible or a visual alarm if the medications are not taken on time and as a secondary mechanism alerting their caregiver if the user has not responded to the alert and taken the medication on time. The system also performs pill inventory management, provides a sealed and secure environment to store medications away from children and unauthorized users, and performs verifications to ensure the correct pill, those that are associated with the correct patient, are the only pills that are stored in the computerized pill intake reminder device such that the patient doesn't accidently take the wrong pill that are not intended for the patient.

The structure of the computerized pill intake reminder device a top housing and a bottom whereby the bottom housing coupled to the top housing such that the top housing can be rotated about the bottom housing to form a closed module. Once closed the medications are protected from outside dust, debris, and thermal conditions that can damage or compromise the medication. The medication in one pouch are also walled from another pouch such that they do not come in contact with one another and any residue is not transferred to another pouch thereby preventing any drug to drug chemical reaction.

The computerized pill intake reminder device includes a processor that is communicatively coupled through an electronic circuit to a plurality of electronic components housed within the pill intake reminder device. These include a speaker, microphone, infrared sensors, cameras, LED lights, microphone, RFID scanner, non-volatile memory, transmitter, and a receiver. Various different colors of LED lights can be used to provide different types of visual alerts.

The speaker is used to sound an audible alarm play an audible message at a specific time to remind the user to take their medication. The device also includes a pill storage module that has an upper and a lower packing plate. The space in between the plates is where the blister pack is inserted.

The device includes a pill detection module. This module includes an infrared sensor (IR) and a camera. In operation, the processor causes the infrared sensor to detect the presence of a pill inside the pouch of the pill/blister pack and the processor causes the camera to quantify the number of pills in the pouch. The pill detection is performed by using a combination of IR Sensors, photodiodes, and a light emitting mechanism. A light beam, or an array of light beams, are passed from one side of the pouch to another and the light that passes through is read by the IR sensors and used for determining whether the pouch includes pills.

The device includes a guidance system to guide the user of the pill intake reminder device to a specific pouch of the pill/blister pack for retrieving pills stored in that pouch. It does so by illuminating a light emitting diode (LED) on or around a specific pouch from which medication/pills are to be retrieved by the user. The guidance system provides a fool-proof method to endure that the user/patient does not accidentally retrieve the wrong pills from another pouch to consumption when its not the time to take those pills. It operates by obtaining the hours of administration (HOA) schedule for the patient and then locating a pouch of the pill/blister pack that correlates with the HOA schedule. Once located, the pouch is illuminated for guidance.

The device includes a display that can be used for providing visual alerts, videos, or recorded messages for instructing the user for taking the pills.

The device uses a transmitter to send alerts to mobile phone for reminding the user to take the medication as well as sending an alert for missing or noncompliance.

The radio frequency identification (RFID) reader is used to verify that a correct pill/blister pack, the one that is associated with the user/patient is being inserted into the device. The verifying process includes scanning an RFID tag located on the blister pack and matching it to stored information in the non-volatile memory of the device or a separate database to ensure that the blister pack matches with the user that is to consume the pills housed in the blister pack Once a match is made, the device is unlocked to allow insertion of the blister pack.

The device also performs periodic inventory of the pills in the blister pack. This includes using an infrared sensor housed within the electronic module to determine the presence of one or more pills in the pouch and using a camera housed underneath the pouch to image and count the number of pills that are in the pouch. The inventory serves as an error check to ensure that the right number of pills from the right pouch were taken by the user at their HOA. The pill inventory system also is used to re-order more medication, if allowed by the prescription, when it detects that it is time to replenish them.

BRIEF DESCRIPTION OF THE DRAWINGS

The accompanying drawings are included to provide further understanding of the invention and constitute a part of the specification. The drawings listed below illustrate embodiments of the invention and, together with the description, serve to explain the principles of the invention, as disclosed by the claims and their equivalents.

FIG. 10A is a block diagram of a column of pouches of a pill pack and a column of IR sensors and cameras used by the pill intake reminder device according to the disclosed embodiments.

FIG. 10B is a detailed view of a single pill pack pouch and IR sensors and cameras used to detect pills in the pouch by the pill intake reminder device according to the disclosed embodiments.

DETAILED DESCRIPTION

Figure 1:
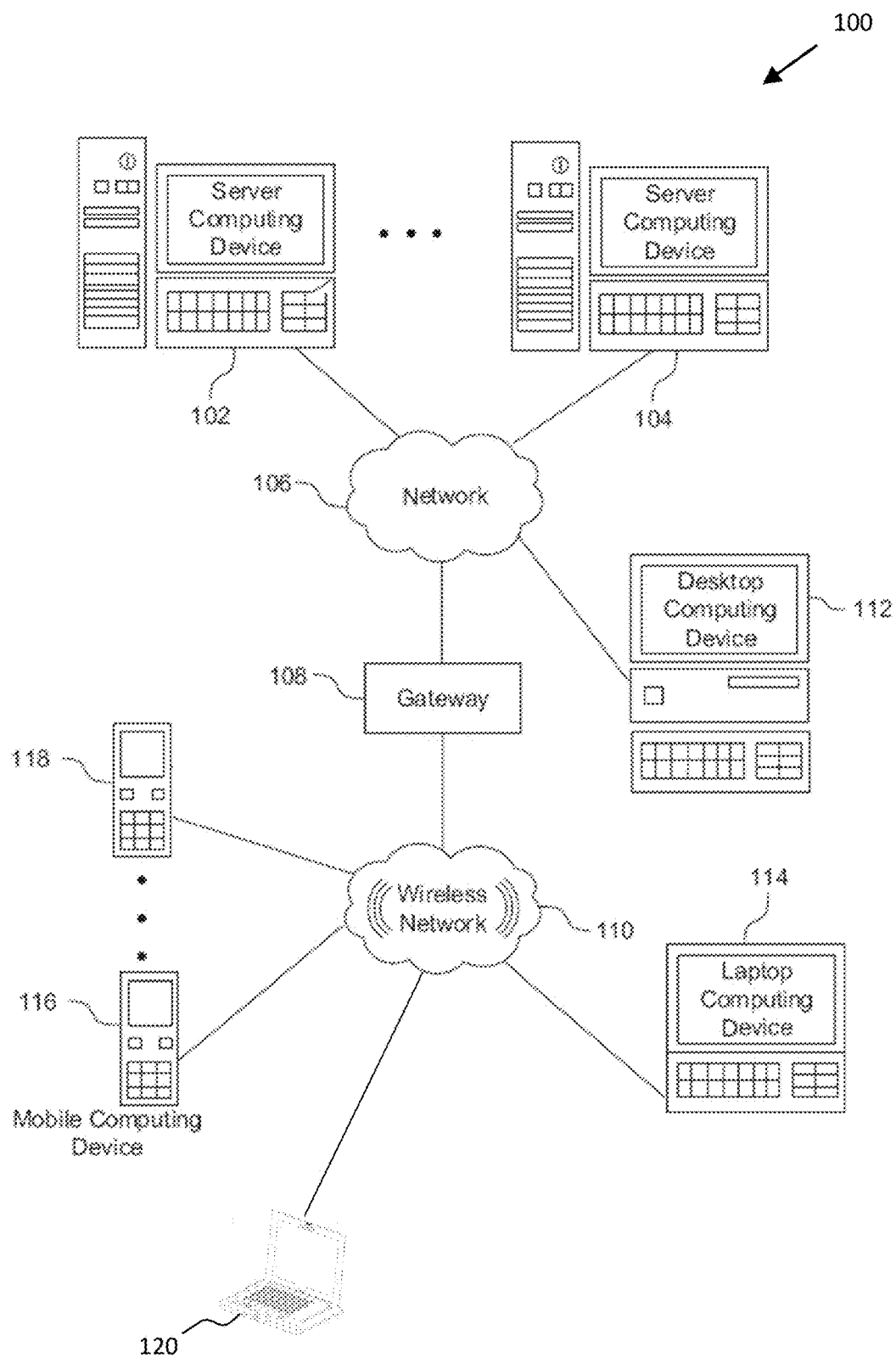
FIG. 1 depicts one embodiment of a system that is used in conjunction with the pill intake reminder device according to the disclosed embodiments.

Aspects of the invention are disclosed in the accompanying description. Alternate embodiments of the present invention and their equivalents are devised without parting from the spirit or scope of the present invention. It should be noted that like elements disclosed below are indicated by like reference numbers in the drawings. While the embodiments discussed below describe a pill intake reminder device that allows deposition of pills into the device, logging and recording of the data associated with the pills, such as hours of administration, alerts the user to take the pills, guides the user to the correct pouch within a pill pack with lighting and audible alerts to simplify obtaining the correct pills at the correct time, and alerts the user, caregiver, and other authorized parties when a non-compliance is detected, and performs scans and inventory check and control using an IR sensor, LED and a camera combination, the methods and embodiments listed are not so limited and equally applicable to other changes in sequence of steps, or use of other comparable embodiments.

FIG. 1 depicts one embodiment of a system that is used in conjunction with the pill intake reminder device according to the disclosed embodiments.

System 100 is used in connection with the pill intake reminder device. The system 100 includes one or more networks, such as a local area networks (LAN) and a wide area network (WAN) shown as network 106. The system 100 also includes wireless network 110 that allows devices in the network to wirelessly communicate with each other after pairing and/or other authorization between the devices.

Gateway 108 is configured to connect remote or different types of networks together, as well as client computing devices 112-120 and server computing devices 102-104.

Client computing devices 112-120 may include any device capable of receiving and sending data over a network, such as wireless network 110. Devices 112-118 may include portable devices such as cellular telephones, smart phones, radio frequency-enabled devices, personal digital assistants, handheld computers, tablets, laptop computers, wearable computers and the like. Device 120 is a pill intake reminder device. Devices 112-120 also may include any computing device that connects to a network using a wired communications medium such as personal computers, multiprocessor systems, microprocessor-based or programmable consumer electronics, network personal computers and the like.

Client computing devices 112-120 also may be web-enabled client devices that include a browser application configured to receive and to send web pages, web-based messages and the like. The browser application may be configured to receive and display graphic, text, multimedia, or the like, employing virtually any web-based language, including a wireless application protocol messages (WAP), or the like.

Client computing devices 112-120 also may include at least one other client application that is configured to receive content from another computing device, including, without limit, server computing devices 102-104. The client application may include a capability to provide and receive textual content, multimedia information, or the like. The client application may further provide information that identifies itself, including a type, capability, name, or the like. In one embodiment, client devices 112-120 may uniquely identify themselves through any of a variety of mechanisms, including a phone number, mobile identification number (MIN), an electronic serial number (ESN), mobile device identifier, network address, such as IP (Internet Protocol) address, media access control (MAC) layer identifier, or other identifier. The identifier may be provided in a message, or the like, sent to another computing device.

Client computing devices 112-120 may also be configured to communicate a message, such as through email, short message service (SMS), multimedia message service (MMS), instant messaging (IM), which may include both video and audio messages to another computing device. Pill intake reminder device 120 (a client computing device) may also receive audio and video messages through the network or wireless network from an authorized user.

Network 106 is configured to couple one or more servers depicted in FIG. 1 as server computing devices 102-104 and their respective components with other computing devices, such as client device 112, and through wireless network 110 to client devices 114-120. Network 106 is enabled to employ any form of computer readable media for communicating information from one electronic device to another. Network 106 also may include the Internet in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router acts as a link between LANs, enabling messages to be sent from one to another. Network 106 may include any communication method by which information may travel between computing devices. Additionally, communication media typically may enable transmission of computer-readable instructions, data structures, program modules, or other types of content, virtually without limit. The above-mentioned system may allow communications between the pill intake reminder device and pharmacy, caregiver, and user's electronic devices, such as a mobile phone, tablet etc. to send alerts.

In yet another configuration, not shown, cloud computing may be used. In such configuration, a cloud computing environment may provide computing devices 102-104 and client devices 114-120 with one or more resources provided by the network environment. The clients and devices may be in communication with the cloud over a network. Clients may include, e.g., thick clients, thin clients, and zero clients. The cloud may also include back end platforms such as servers or data centers. The cloud may be public, private, or hybrid.

Figure 2A:
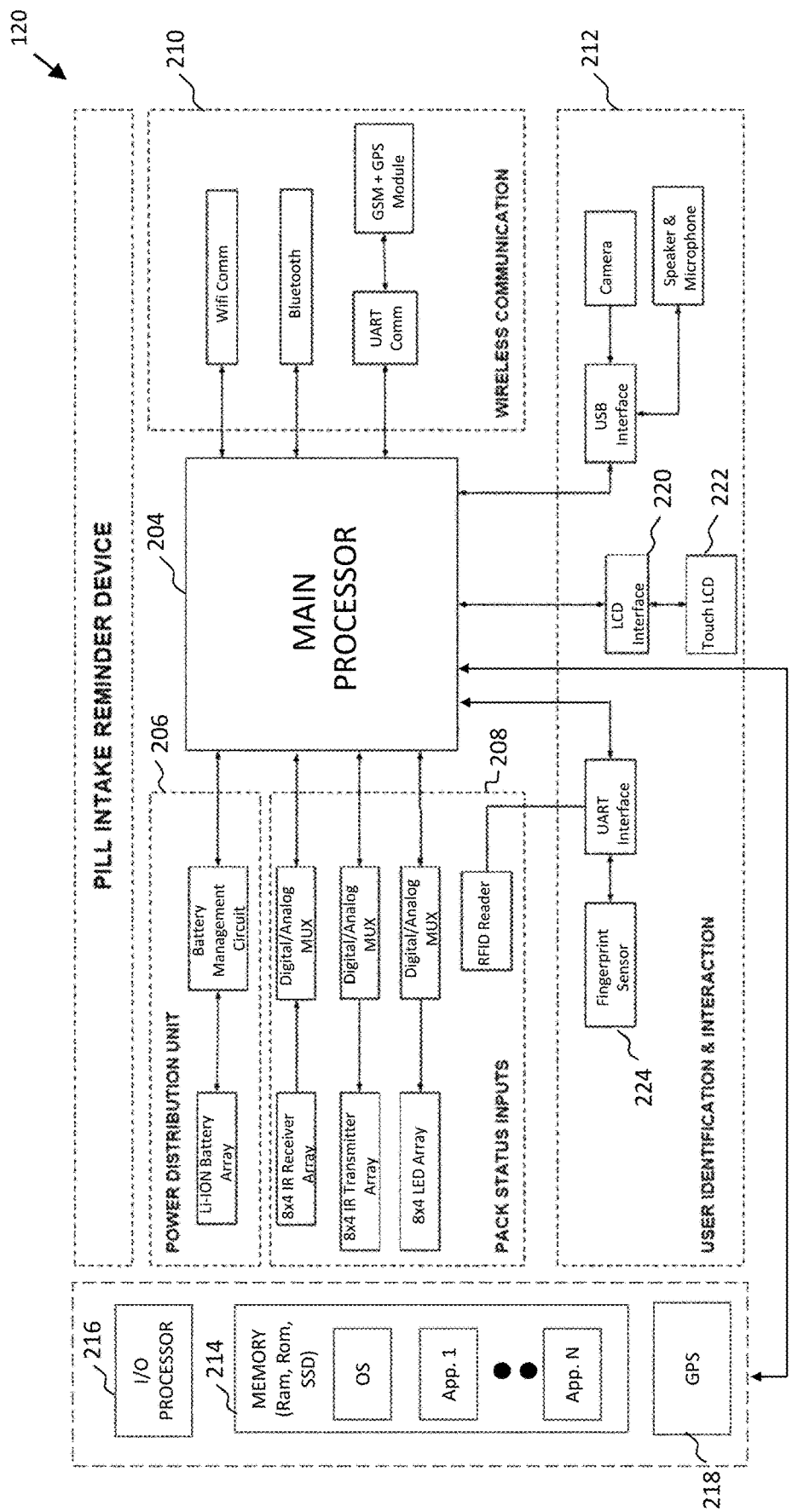
FIG. 2A illustrates a block diagram of some of the hardware components of the pill intake reminder device according to the disclosed embodiments.

FIG. 2A depicts a pill intake reminder device 120 configured to execute the functionality disclosed in greater detail below. Pill intake reminder device 120 may communicate with other devices over system 100 to perform the functions needed for the reminding the user to take their medications and alerting a caregiver if non-compliance is detected. The functions further include providing audible and visual alerts before the time to take the medication, alerts at the time of administration, post alarms after the time to take the medication has passed, and notification to the caregiver or authorized person of the non-compliance. The audible and visual alerts may either be on the pill intake reminder device using the display and speaker areas, or on an electronic device connected to the pill intake reminder device, such as a mobile phone, table, personal computer, or both. Additionally, functions also include verification of a pill pack before placement into the pill intake reminder device and performing scans and inventory check and control using an IR sensor, LED and a camera combination.

The pill intake reminder device 120 may be connected to a server, desktop computer, laptop computer, tablet computer, or smartphone. In some examples, pill intake reminder device 120 may be connected to a cloud computing node. Pill intake reminder device 120 may be described in the general context of computer system executable instructions, such as program modules, being executed by a computer system. Generally, program modules may include routines, programs, objects, components, logic, data structures, and so on that perform particular tasks or implement particular abstract data types. Pill intake reminder device 120 may be practiced in distributed cloud computing environments where tasks are performed by remote processing devices that are linked through a communications network. In a distributed cloud computing environment, program modules may be located in both local and remote computer system storage media including memory storage devices.

The pill intake reminder device 120 includes a main processor 204 and memory module 206, display interface 214. It further includes a power distribution unit 206, a pack status inputs unit 208, a wireless communications module 210, user identification and interaction module 212, memory 214, and an I/O processor 216, and a global positioning system (GPS) 218.

The main processor 204 is adapted to execute stored instructions, the memory module 214 to provide memory space for operations of said instructions during operation. The processor 204 can be a single-core processor, multi-core processor, computing cluster, or any number of other configurations. The memory 214 can include random access memory (RAM), read only memory, flash memory, or any other suitable memory systems. The memory module may store applications 1 through N that may be used to manage the pill intake reminder device. The memory may also store information relating to the adherence of the pills being retrieved form the pill intake reminder device. For example, specific pills are to be retrieved and consumed at a prescribed time for the user. If the user retrieves the pills at prescribed time, later than the prescribed time, or forgets to take them at all, the pill intake reminder device collects the adherence data and stores such data into the memory. The data may be used for providing to authorized users, doctors etc.

The processor 204 may be connected through a system interconnect (e.g., PCI®, PCI-Express®, etc.) to an input/output (I/O) device interface adapted to connect the pill intake reminder device 120 to one or more I/O devices. The I/O devices 110 may include, for example, a keyboard, camera, sensor, a touchpad, fingerprint scanner, fingerprint sensor, alarm, or a touchscreen, among others. The I/O devices may be built-in components of the pill intake reminder device 120 may be devices that are externally connected to the pill intake reminder device 120.

The processor 204 may also be linked through the system interconnect to a display interface adapted to connect the pill intake reminder device 120 to a display device 114. The display device 114 may include a display screen that is a built-in component of the pill intake reminder device, such as an LCD interface 220 or a touch LCD 222. The display device may also include a computer monitor, television, or projector, among others, that is externally connected to the pill intake reminder device 120. In addition, a network interface controller (NIC) may be adapted to connect the pill intake reminder device 120 through the system interconnect to the wireless network 210. The network 210 may be a cellular network, a radio network, a wide area network (WAN), a local area network (LAN), or the Internet, among others. A remote server may connect to the pill intake reminder device 120 through the network 210. In some examples, the remote server can send an authentication request for a transaction to the pill intake reminder device 120.

The processor 204 may also be linked through the system interconnect to memory or a storage device that can include a hard drive, an optical drive, a USB flash drive, an array of drives, or any combinations thereof.

It is to be understood that the block diagram of FIG. 2A is not intended to indicate that the pill intake reminder device 120 is to include all of the components shown in FIG. 2A. Rather, the pill intake reminder device 120 can include fewer or additional components not illustrated in FIG. 2A (e.g., additional memory components, embedded controllers, modules, additional network interfaces, etc.). Furthermore, any of the functionalities of the pill intake reminder device 120 may be partially, or entirely, implemented in hardware and/or in the processor 204. For example, the functionality may be implemented with an application specific integrated circuit, logic implemented in an embedded controller, or in logic implemented in the processor 204, among others.

Figure 2B:
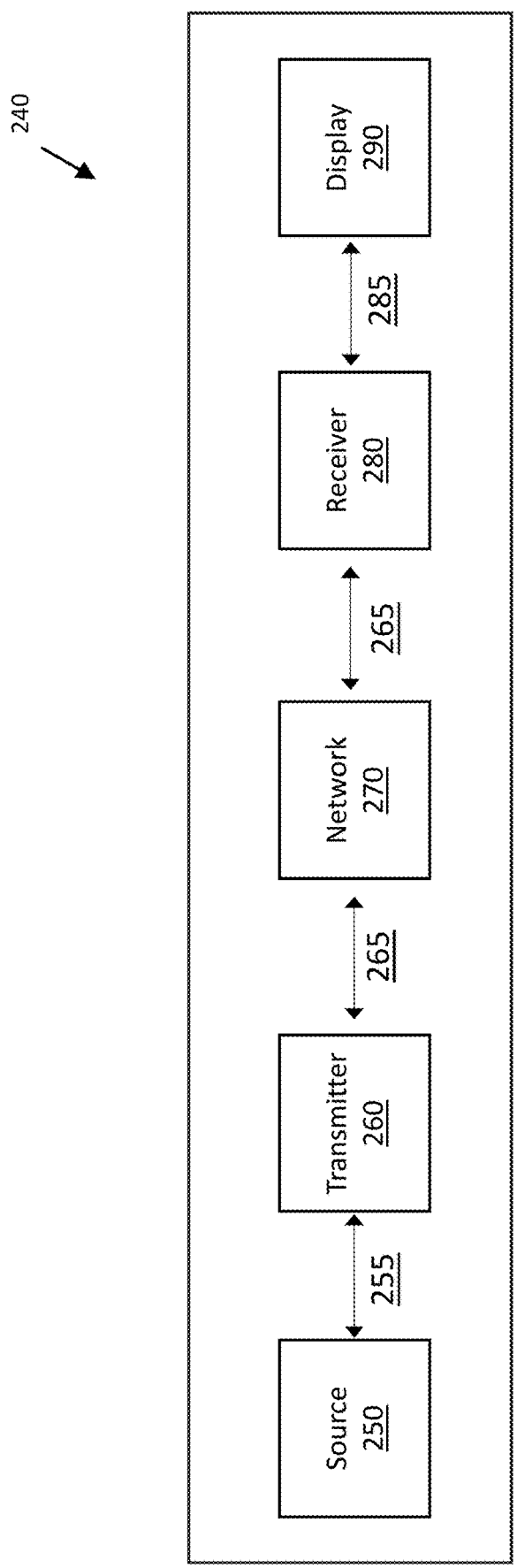
FIG. 2B illustrates a block diagram of some of the hardware components of the pill intake reminder device for transmitting and receiving signals according to the disclosed embodiments.

FIG. 2B illustrates some of the hardware components of the pill intake reminder device for transmitting and receiving signals according to the disclosed embodiments.

System 240 comprises a source 250 coupled to a transmitter 260 via link 255. Transmitter 260 is coupled to receiver 280 via link 265 on network 270. Receiver 280 is coupled to display 290 via link 285. The system 240 provides communication in and out of the pill intake reminder device 120 to provide messages, images, videos, and audible sounds to the user.

Figure 3:
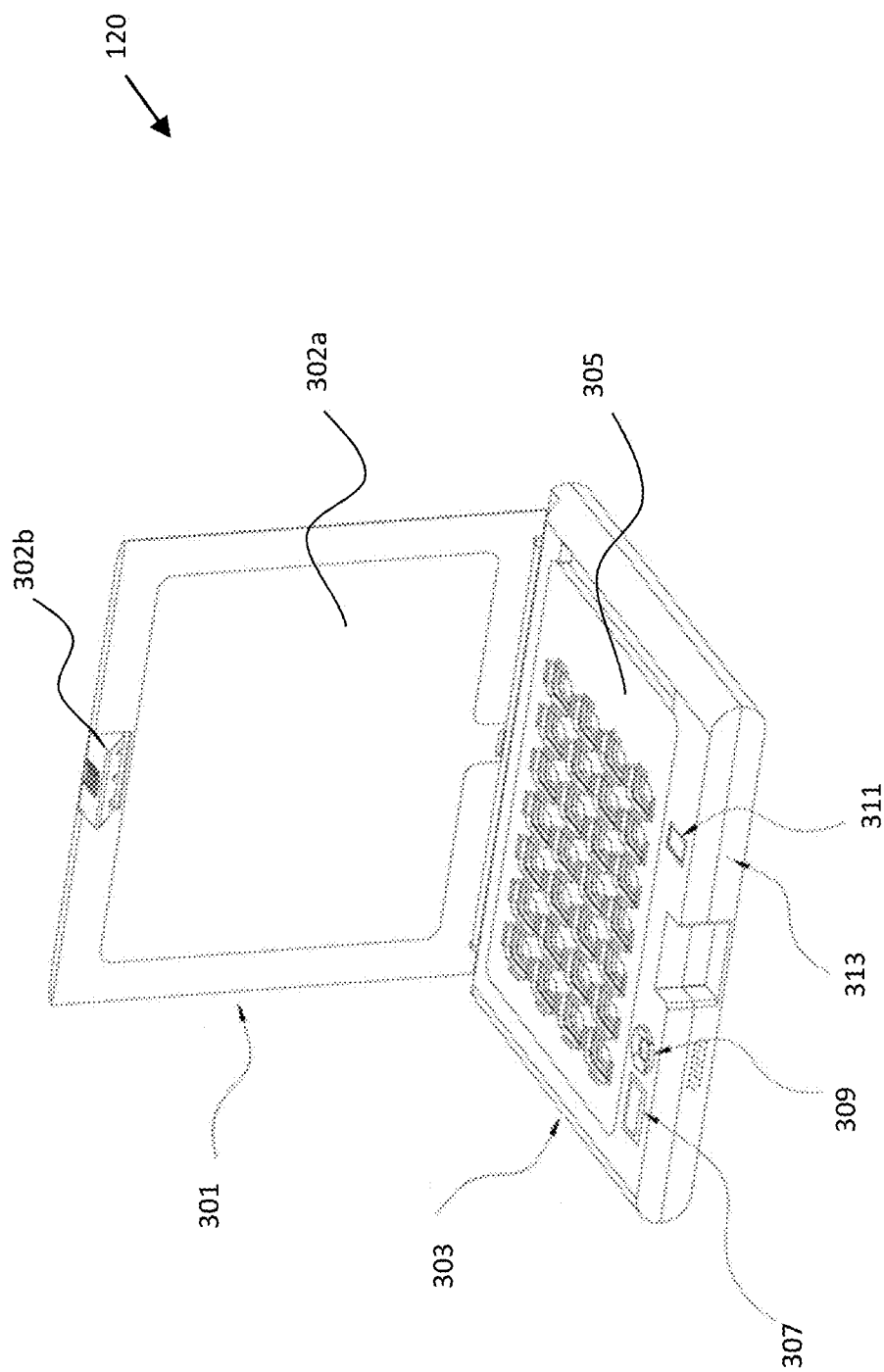
FIG. 3 is an isometric view of the pill intake reminder device in its open position according to the disclosed embodiments.

FIG. 3 is an isometric view of the pill intake reminder device in its open position according to the disclosed embodiments. The pill intake reminder device 120 acts to remind its users to take their pills in a timely manner, which means at a prescribed hour of administration. It holds the medication in its pouches in accordance with this hour or administration.

Hours of administration or HOA are times of the day or week when a medication is to be administered. For example, the HOA can be on a specific day of the week, every day, or multiple times a day, or only at a certain time of day that is before or after a meal; it all depends on the specific patient and what a medical professional has prescribed for them. Since taking a wrong pill or a wrong dosage can be dangerous to health, it is important that the pills are taken correctly and the patient understand the right way to administer them and the risks associated with them. The provided instructions by the pharmacist or the medical profession regarding the HOA should be strictly followed. Some medication may have a longer window of administration while some may have a shorter window. In some cases, the HOA is at a specific time or within a specific time window. This is because, to be effective, pills need to reach a certain level in your bloodstream and as such need to be given at specific times, such as every morning, to keep that amount of drug in your system. Taking a medication too soon could lead to drug levels that are too high, while on the contrary, missing a dose or not taking it at time could lower the amount of drug in your body and keep it from working properly. HOA's are designed to manage these risks and allow the medication to properly take its effect in the body.

A pill pack is typically organized by hours of administration (HOA) that includes, for example, the amount of a first drug that is to be administered to a patient in a morning time slot, the amount of a second drug that is to be administered to the patient in the same or different time slot.

The pill intake reminder device 120 includes a top housing 301 and a bottom housing 303. The top housing 301 may include an inside piece, a protrusion, or a liner 302a that fits snugly into the bottom housing 303 when the top housing 301 is pivoted and closed onto the bottom housing. The inside liner 302a may be of a certain material that is recommended for providing certain encapsulation and sealing of medication such that it protects the medications from dust, and temperature variations. For example, certain aluminum, thermoformed plastics, or heat shielding materials may also be used.

In an alternative embodiment, the space shown as 302a may be used as a display. The display may be used to play videos, provide visual instructions and guidance, or depict the pouch from which a pill is to be retrieved. It may also be used to show details of the pill that is to be taken and its side effects or other pill related information such as expiry date. Additionally, for patients that are deaf, the display may be used to visually guide them through sign language so they may take their pills appropriately. The system has the capability of converting written text and voice recorded messages to visual depictions in sign language.

The top housing 301 also includes a latch or locking mechanism 302b that is used when the top housing 301 is to be locked with the bottom housing 303.

The bottom housing 303 includes a pill storage and detection module 305, a user or display screen 307, a keypad 309, a fingerprint scanner 311, and a microphone 313.

The pill intake reminder device 120 includes a pill storage and detection module 305. The function of the pill storage and detection module is multifold, to store medication/pills, to detect the presence of the pills, to determine the count of the pills, and act as a guiding mechanism for the user to retrieve the correct pills for the hour of administration. The pill storage and detection module 305 includes LED (light emitting diodes) or other lighting as well as IR sensors for it to perform its detection and guidance functions. More details on the pill storage and detection module 305 are provided in FIG. 10A.

The display screen 307, also referred to as the user screen, displays the status of the pill intake reminder device 120. For example, the display screen 307 may show instructions when it's time to take a certain pill that has been placed inside the pill intake reminder device 120 or show a certain type of colored light to help guide the user to select the pouch with the similar colored light. The display screen may also show recorded messages, videos, or other type of alerts that are either associated with the medication or specific to the user in aiding them to take their medication.

The keypad 309 is a standard QWERTY keypad used for entering data into the pill intake reminder device 120. Alternatively, a smaller keypad or a keypad with a limited predefined function is also contemplated. The keypad 309 may be used by the user, caregiver, a relative, or any authorized individual in inputting text that will help the user when taking the medication. The keypad may also be used to set a reminder, select a type of alarm, or many other interact and select many other features of the pill intake reminder device 120.

The pill intake reminder device 120 includes a finger print scanner 309. Since access to medication and authorized use and intake of medication is utterly important, the fingerprint scanner's function is to verify an individual's fingerprint against a stored fingerprint in the system.

In operation, a user of the system uploads his/her fingerprint into the memory of the pill intake reminder device 120. A detailed scan of the unique ridges and furrows on a finger that define the individual's unique fingerprint is obtained and uploaded. At the time of use, the user places their finger on the scanner and the processor causes the activation of a finger print sensor 224 that is part of the fingerprint scanner, the processor then processes the scanned image. The processor then recognizes the biometrics that are unique characteristics of authorized user. It does so by scanning the unique ridges and furrows on a finger and matching them with the stored version in the memory.

Disregarding minor changes, such as cuts, oil/grease on fingers, the finger print scanner confirms that there are enough matching components and then authorizes used the use of the pill intake reminder device 120. In some instances, the user can require a certain threshold, such as a 90% match, to occur before allowing the user to open the pill intake reminder device 120.

The microphone 313 is located in the bottom housing 303 of the pill intake reminder device 120. The user of the system can use the microphone 313 to record messages. The caregiver may also record messages for the user using the microphone 120.

The voice recording may be heard through a speaker located in the bottom hosing 303 of the pill intake reminder device 120. The messages, either by the user, the caregiver, or any authorized individual may relate to the medications stored inside the pill storage and detection module 305. For example, a caregiver may record instructions on when to take a certain pill or whether to take the pill before, during, or after a meal. A caregiver, or the user, may also chose to verbally record the instructions provided by the doctor, pharmacist, or a medical professional on any details related to the taking of medication. The pill intake reminder device may also include capability to transform a text message to audible speech, including having the ability to translate text from one language to another. For example, a doctor or caregiver giving instructions in English can be translated to another language, such as Spanish or French, that may be suitable for the user and the translated text may be audibly heard through the speaker.

The microphone may also be connected to a speech recognition unit converts voice to text. This may be useful if a written message is to be sent to a caregiver or displayed to the user. The user of the system may choose to voice record a message, such a message relating to the administering of the pills, and have it displayed on the screen. The text to voice feature helps those that need glasses, visually impaired, or simply are in a place that is not well lit to be able to follow the instructions audibly without having a need to read anything.

Figure 4:
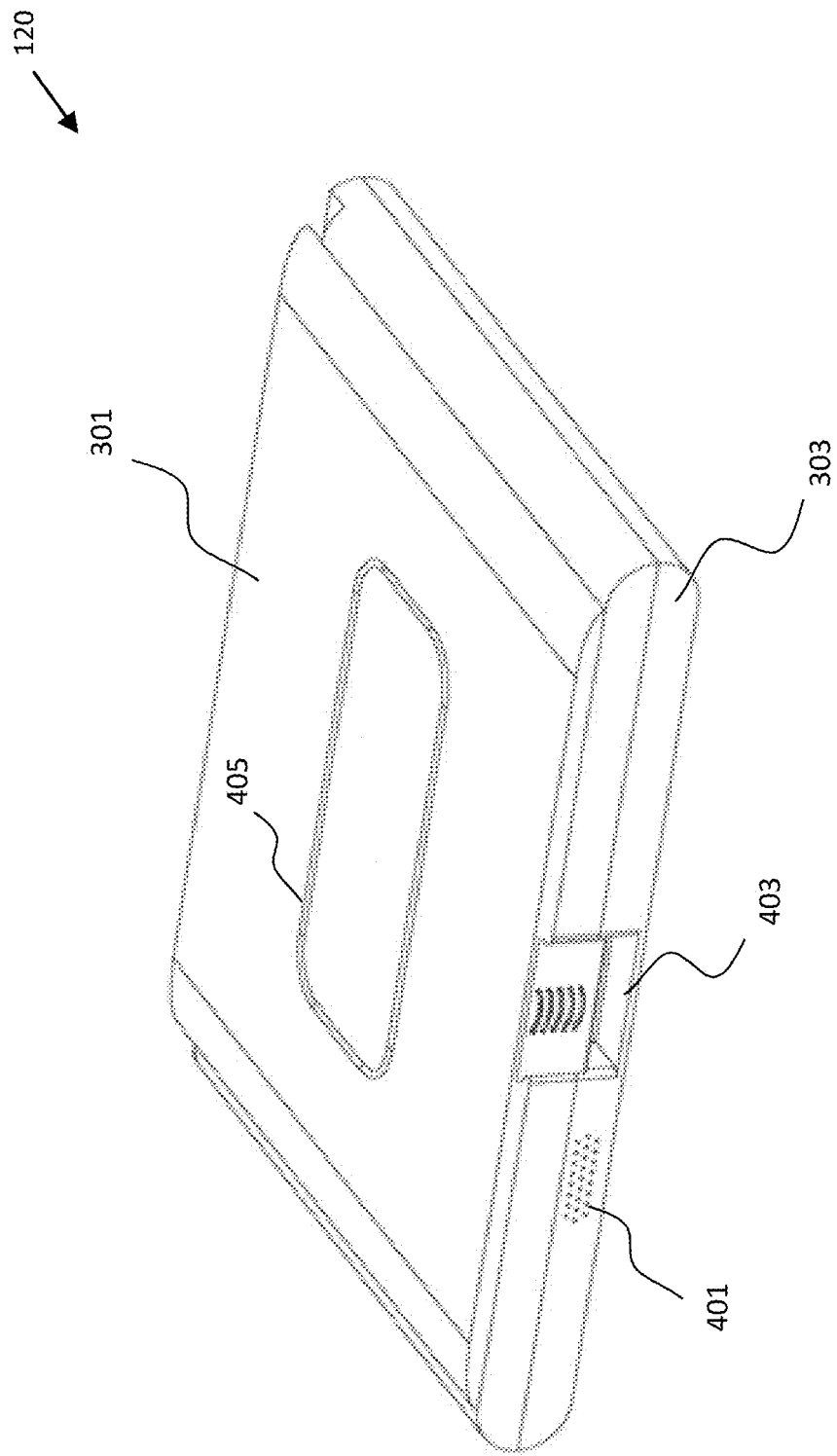
FIG. 4 is an isometric view of the pill intake reminder device in its closed position according to the disclosed embodiments.

FIG. 4 is an isometric view of the pill intake reminder device in its closed position according to the disclosed embodiments. The pill intake reminder device 120 includes a top housing 301 and a bottom housing 303. The bottom housing includes a speaker 401.

The speaker 401 provide audio sound that may include an alarm, a recorded message, or some other type of audio alert. The speaker may also be used by an authorized third party to send a voice note or communicate with the patient through the speaker.

When the speaker is used for an alarm, the pill intake reminder device 120 may send an audio sound, such as a beep, bell, or some musical tune that is either selected for by the pill intake reminder device 120 or can be selected by the user of the pill intake reminder device 120. For example, multiple alarms may also be programmed and played through the speaker. In one instance a user can have an alarm set to sound at an interval before the actual time for taking the medication, a secondary alarm that is set to sound if the pill intake reminder device 120 was not opened in time, i.e., after the time for the intake of the medicine has passed, or other custom alarms before and after the time at which the medication is to be taken. The user may also select from a variety of audible sounds for the alarm. The sounds may be similar or differ from each other for each separate alarm. As mentioned above, the user, a caregiver, or an authorized individual may also record their voice and instructions that can be played by the speaker.

The bottom housing 303 of the pill intake reminder device 120 also includes a lock 403. The lock 403 includes mechanical mechanisms, such as a latch, that allows the user to open, close, and lock the pill intake reminder device 120. Alternatively, the lock 403 may also include electronic and other means that allow opening, closing, and locking of the pill intake reminder device 120. These electronic and other means may allow opening though voice activation, a remote-control device, fingerprint scanning, or by input though a keypad or a passcode to allow opening and locking of the pill intake reminder device 120.

The top housing 301 of the pill intake reminder device 120 also includes a light display area 405. As mentioned above, the pill intake reminder device 120 includes an audio alarm. In its closed position, the light display area 405 acts in a similar manner to the alarm but to provide a visual alarm instead.

In this embodiment, the light display area 405 can be a thin light defined by a thick line of light that is somewhat rectangular in shape. Alternatively, the light display area 405 can be of other shapes, such as a circle, triangle, or other custom shape. It may also be a wide area, such as a rectangle covering a larger amount of space on the outside of the housing instead of a thinner line of light.

The light display area 405 may use an LED. Alternatively, the light display area 405 may use other means to light up the light display area 405.

The light may be of different colors and each color may correlate with a specific type of alarm. For example, a color scheme, such as green, yellow, and red may be used to inform the user of the amount of time left to take the medication. A green light may indicate that it is time to take the medication, a yellow light may indicate that the time to take the medication has passed, and a red light may indicate a final warning or a high alert to take the medication as it may be getting too late to take it. Alternatively, just one type of light may be used to visually alert the user for taking the medication. Similar, to the audio alert, the user may choose the timing for the lights to provide a visual alarm, including colors of light and multiple alarms at a spread out sequential time. The user of the pill intake reminder device 120 may also program or customize the type of visual alarm by selecting the timing of the alarm, type of display, color of light, and the duration of the alarm.

As it can be seen in FIG. 4, the pill intake reminder device 120 is portable and can fit in a user's purse, backpack, or a computer size bag. The pill intake reminder device 120, regardless of its orientation, whether upright, right side up, or upside down, will retain the medications within and its orientation will not damage or allow the medications to leave their respective storage chambers within the pill intake reminder device 120.

Figure 5:
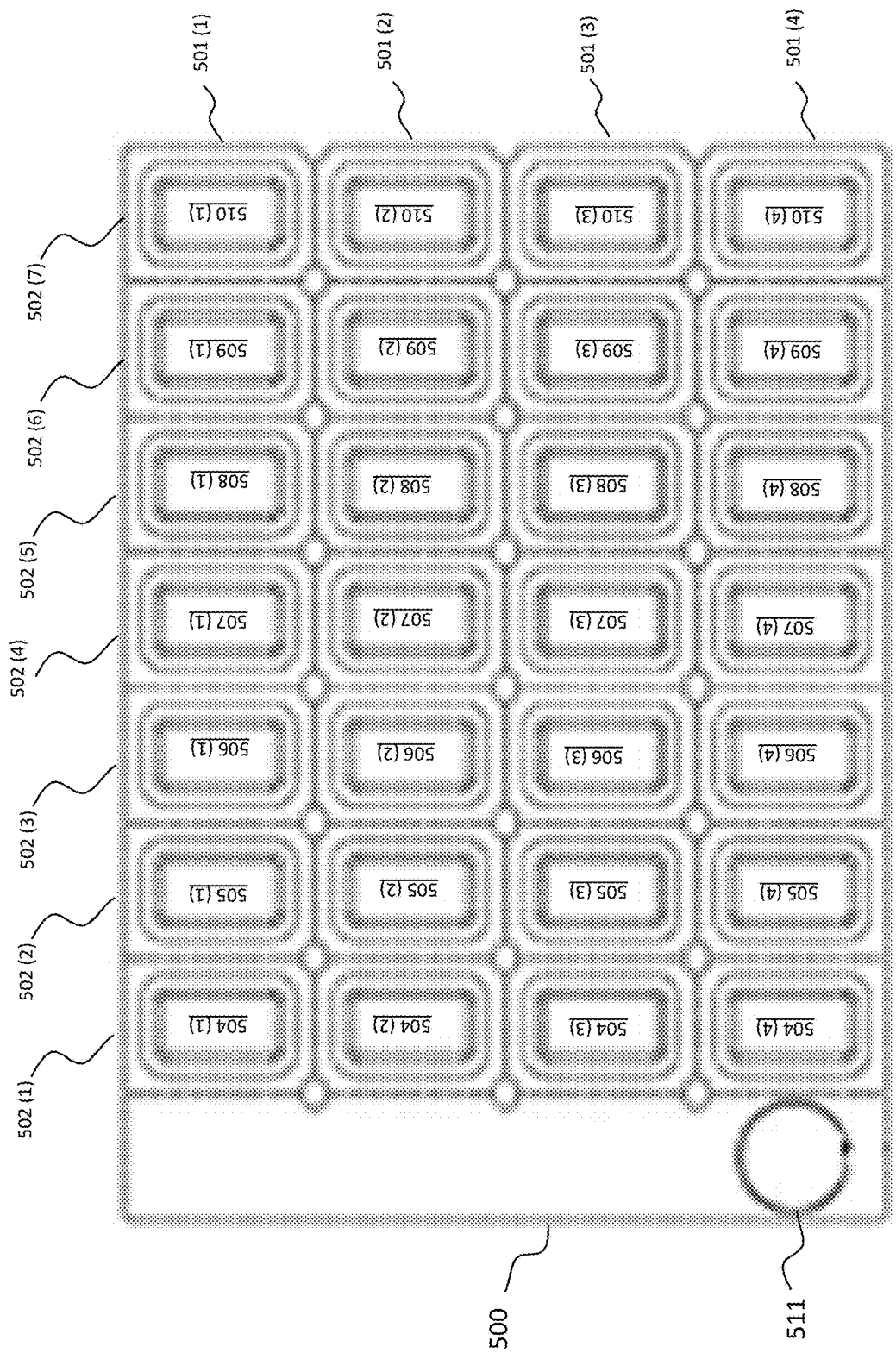
FIG. 5 is a top view of a pill pack (or blister pack) that is used in conjunction with the pill intake reminder device according to the disclosed embodiments.

FIG. 5 is a top view of a pill pack (or blister pack) that is used in conjunction with the pill intake reminder device according to the disclosed embodiments. Pill pack 500 includes a plurality of chambers (also referred to as pouches or slots) that are configured to receive pills. Chambers or Slots 504 (1)-510(4) are arranged in rows 501(1)-501(4) and columns 502(1)-502(7). It is noted that the number of rows and columns are shown for explanatory purposes only, and the actual implementation can have additional, or fewer rows and/or columns, as desired.

The slots 504 (1)-510(4) of pill pack 500 are configured to receive several pills of the same or different types. This can be implemented in one of several ways. In some implementations, only one pill is deposited in each slot of the pill pack 500. However, in other implementations, several pills are deposited in one or more slots of the pill pack 500.

In some embodiments, the medications are dispensed by day slots in rows 501 (1) to 501 (4). For example, the pill pack can be divided as such, 501 (1) is for morning, 501 (2) is for afternoon, 501 (3) is for evening, and 501 (4) is for night. Accordingly, pills that are to be consumed in the morning will be located in the slot 501 (1).

In some embodiments, the medications are dispensed by days of the week slots in columns 502 (1) to 502 (7). For example, the pill pack can be divided as such, 502 (1) is for Monday, 502 (2) is for Tuesday, 502 (3) is for Wednesday, 502 (4) is for Thursday, 502 (5) is for Friday, 502 (6) is for Saturday, and 502 (7) is for Sunday. Accordingly, pills that are to be consumed on Friday can be found in column 501 (6).

A cross matching of a particular row and a column provides the exact day of the week and the time a pill is to be consumed. For example, pills that are to be take on Thursday morning can be found by cross referencing column 502 (4) and row 501 (1) such that they can be located in slot 507(1) Likewise, pills that are to be taken on Sunday night can be by cross referencing column 502 (7) and row 501 (4) such that they can be located in slot 510(4).

Rows and time slots columns in the pill pack 500 are created according to the information provided by the patient, caregiver, pharmacy, doctor etc. The time slots are created horizontally to enable the patient to take his or her medication based on the preferred schedule. Of course, the columns and rows may be swapped so that the columns represent days and the rows represent times.

In one embodiment, the slots of the pill pack 500 are square in shape. All the slots in the pill pack 500 are of the same exact dimensions. Alternatively, the slots may be of other shapes and vary in dimensions from other slots in the pill pack 500. Further, the slots may also include movable members that allow each slot to be individually adjusted for size and shape as desired. Other alternatives such as adjusting an entire row or column of slots or increasing or decreasing the number of slots is alto contemplated.

The pill pack 500 also includes a radio frequency identification tag (RFID tag) 511. The RFID tag 511 contains patient information, such as patient name, birth date, types of prescriptions and pills designated for the patient and other patient data relevant and needed by the pharmacies or the system to operate. The pill intake reminder device 600 checks and verifies the RFID tag 511 on the pill pack 500 prior to allowing the pills inside the pill pack 505 to be populate into the chambers of the pill intake reminder device 120. The RFID assurance check ensures that the correct pills that are designated for the right patient are being deposited in the correct pill pack that is designated for the patient. Quality assurance and verification through such RFID check minimizes and error and accidental mishaps, such as a wrong medication being provided to the wrong patient or deposition of a morning medicine accidentally in the evening slot.

Figure 6:
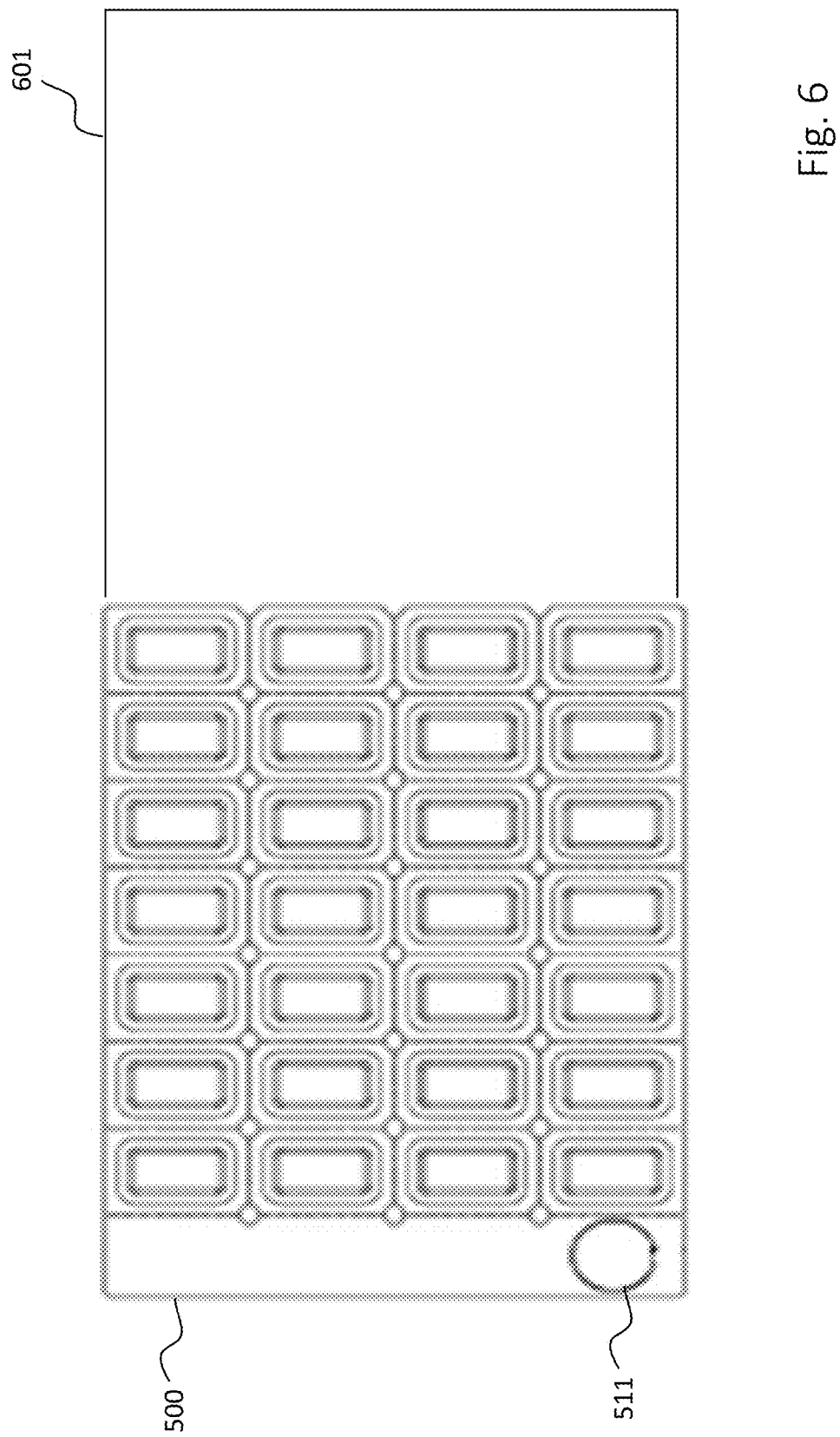
FIG. 6 is a top view of a pill pack (or blister pack) along with a printed label attached to the pill pack that is used in conjunction with the pill intake reminder device according to the disclosed embodiments.

FIG. 6 is a top view of a pill pack (or blister pack) along with a printed label attached to the pill pack that is used in conjunction with the pill intake reminder device according to the disclosed embodiments.

The label is a printed portion of the pill pack 500 that extends from the main body of the pill pack 500. The label 601 includes patient information, such as patient name, birth date, types of prescriptions and pills designated for the patient and other patient data relevant to the medication inside the pill pack 505. The information can be changed to other patient, medication, or hours of administration (HOA) data that may be required to meet regulatory compliance. The label 601 allows easy read of the contents inside the pill pack 500 by the user, patient, caregiver, pharmacy or doctor, while the RFID tag 511 is imbedded data that can only be read by an RFID reader.

The label 601 can be folded either on top or the bottom of the pill pack 500. In one embodiment, the label 601 is printed by a robot. The printed label includes the patient data as well as data relating to the medication inside the pill pack 500. One end of the label 601 can be removably attached to the top of the pill pack 500 while the other end is attached at the end of the pill pack 500 as shown. The removably attached end of the label 601 can be removed by applying a small force and the end can then be flapped over to the bottom of the pill pack 500 or another receptacle.

The label 601 is a paper on which the printing is done. The label 601 can also be a flexible thin sheet of plastic. The label 601 includes a header which has the information on the medication enclosed within the pill pack 500.

Figure 7:
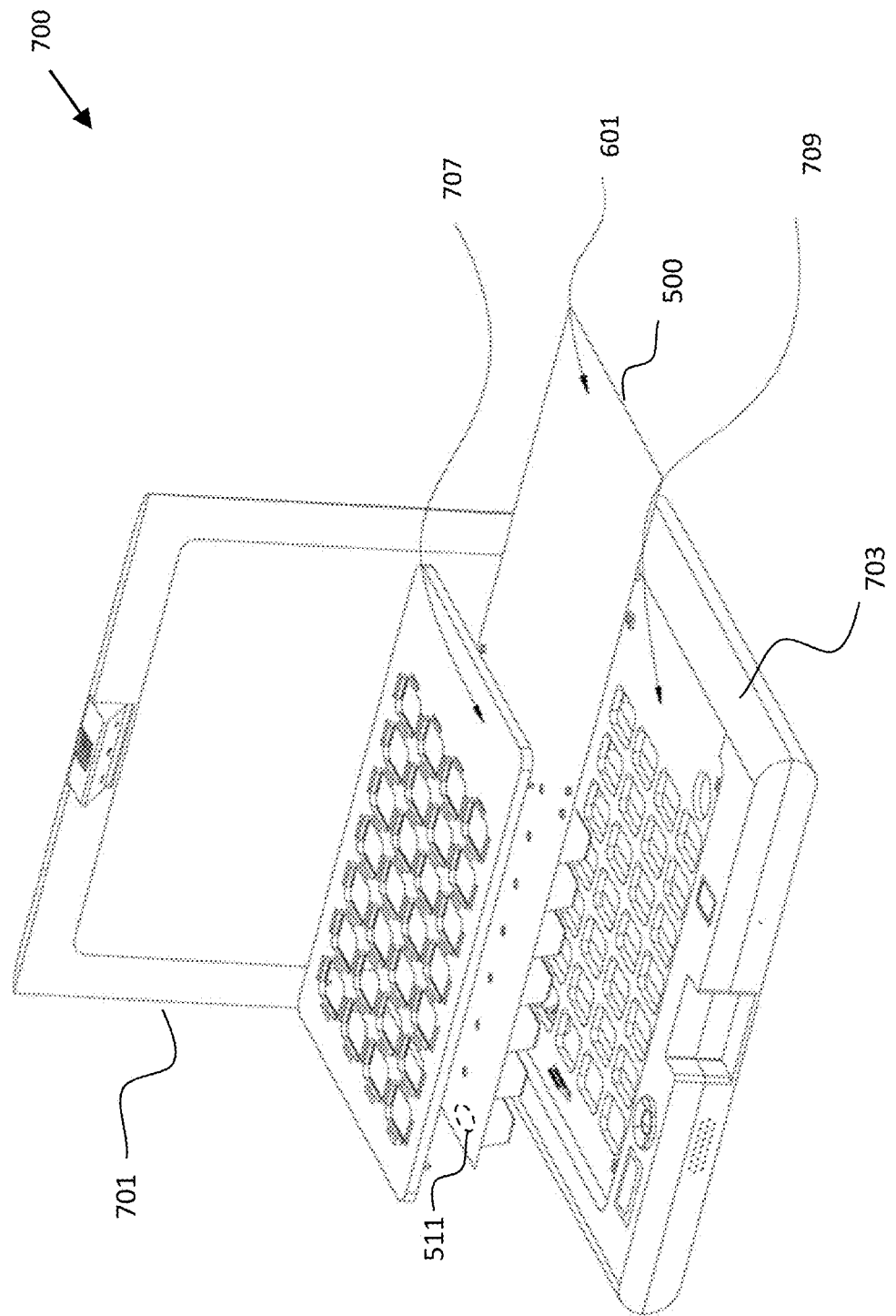
FIG. 7 is an exploded view of the pill intake reminder device and some of its components, such as the packing plates, used by the pill intake reminder device according to the disclosed embodiments.

FIG. 7 is an exploded view of the pill intake reminder device and some of its components, such as the packing plates, used by the pill intake reminder device according to the disclosed embodiments.

The pill intake reminder device 700 includes an upper housing 701, a lower housing 703, and plurality of components that are part of pill intake reminder device 700. The figure also depicts some components, such as a pill pack, that can be inserted into the lower housing 703.

In one embodiment, the bottom housing 703 includes a combination of packing plates. It includes an upper packing plate 707 and a lower packing plate 709. A pill pack 705 can be inserted in-between the upper packing plate 707 and a lower packing plate 709.

The upper packing plate 707 includes a plurality of cut-outs, holes, or perforations. The layout of the holes resembles the layout of the pouches (also referred to earlier as chambers or slots) in the pill pack 500. The shape of the holes in the upper packing plate 707 also resembles the shape of the pouches of the pill pack 500. The upper packing plate 707 holes overlay the pill pack 500 such that each pouch of the pill pack 500 is overlaid by a hole of the upper pack plate 707 such that a user of the pill intake reminder device 700 can access each pouch of the pill pack 500. In operation, a user will insert their finger through a desired or suggested hole of the upper pack plate 707 to access the pills in a particular pouch of the pill pack 500.

The upper pack plate 707 also includes a plurality of lights, such as light emitting diodes (LEDs). Alternatively, other types of lighting, such as LCD or CFL are also contemplated. Each structure surrounding each hole of the upper pack plate 707 includes a certain thickness and the lighting is placed such that it illuminates that thickness. The LEDs may be of various colors and brightness. The color scheme may be automated to customized. In one embodiment, a green, orange and red color scheme may be used while in another embodiment, different colors to signify the time of day may also be used.

The LEDs may be programmed to light up and brightly illuminate a particular hole, i.e. the thickness space around the hole, to alert the user of the pill intake reminder device 700 that it's time to retrieve the pills that are in a pouch that is located underneath the illuminated hole. The mechanism visually aids the user by identifying the correct pouch at the correct time to take the medication in that pouch. The mechanism acts to prevent errors made, such as errors made by senior citizens, patient that are incapable of reading or in a hurry, to direct them visually such that they do not accidentally take the wrong pills from the wrong pouch at the wrong time.

The upper pack plate 707 includes a plurality of sensors. Each sensor is associated with a hole of the upper pack plate 707. The sensors detect the insertion of a finger, or other means, through the hole of the upper pack plate 707 and record the event as an attempt to retrieve the medication for a specific pouch.

The lower packing plate 709 also includes a plurality of cut-outs, holes, or perforations. The layout of the holes resembles the layout of the pouches (also referred to earlier as chambers or slots) in the pill pack 500. The shape of the holes in the lower packing plate 709 also resembles the shape of the pouches of the pill pack 500. In the layout of the upper packing plate 707, the pill pack 500, and the lower packing plate 709, the lower packing plate 709 sits below at the bottom and underneath the pill pack 500.

The holes in the lower packing plate 709 allow the insertion of the pill pack 500 such that each pouch of the pill pack 500 is inserted through a hole of the lower packing plate 709. In operation, a user will insert their finger through a desired or suggested hole of the upper pack plate 707 and therethrough into a pouch of the pill pack 500. Since the pouches are transparent and inserted inside the hole of the lower packing plate 709, the user's finger would pass through the hole of the lower packing plate 709 while its inside the pill pack pouch to retrieve the pills in that pouch.

In an alternative embodiment, the holes in the lower packing plate 709 allow the insertion of the pill pack 500 such that each column of pouches of the pill pack 500 are inserted through a column of openings of the lower packing plate 709.

The lower packing plate 709 also includes sensors. These sensors detect the presence of a pill inside the pouches of the pill pack 500. Since the pill pack pouch is transparent, each sensor detects whether the pouch is empty or if any contents remain in the pouch. The sensors are connected to the system, as shown in FIG. 1, and processors and architectural layout, as shown in FIG. 2, that operate the pill intake reminder device 700. The sensors communicate the information for each pouch, i.e. whether empty or some pill detected to the pill intake reminder device 700 for further processing.

Figure 8:
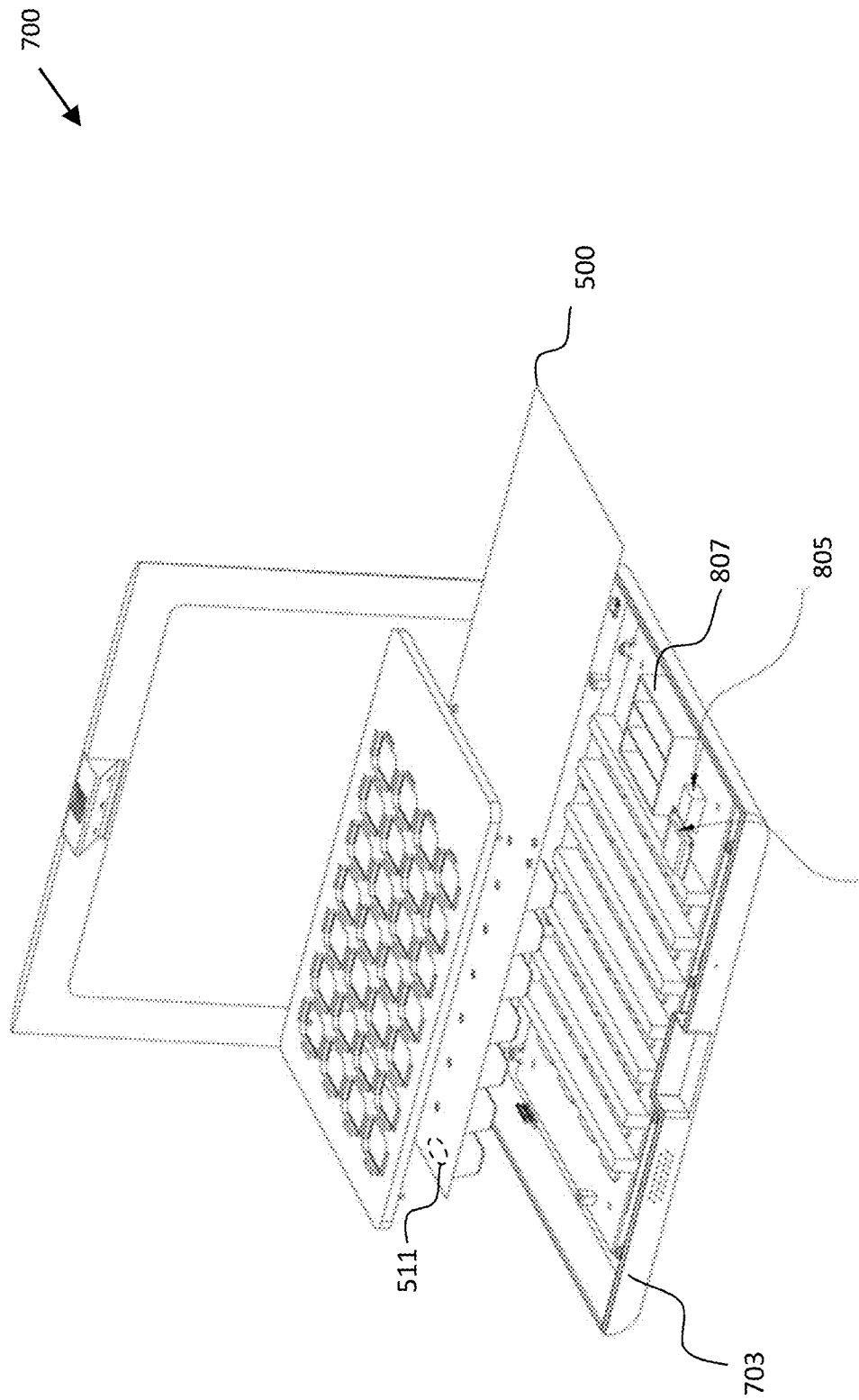
FIG. 8 is an exploded view of the pill intake reminder device and some of its components, such as an RFID reader, used by the pill intake reminder device according to the disclosed embodiments.

FIG. 8 is an exploded view of the pill intake reminder device and an RFID reader and a plurality of components used by the pill intake reminder device according to the disclosed embodiments. The pill intake reminder device 700 includes a bottom housing 703 that further includes a radio frequency identification reader 801 (RFID reader 801) and a Wifi/SIM connectivity circuit 803.

The RFID reader 801 checks the RFID tag 511 of the pill pack 500 to ensure that the correct pill pack is being inserted in the pill intake reminder device 700. In operation, the RFID reader 801 in bottom housing 703 is used for reading and verifying the RFID tag 511 of the pill pack 500. When a new pill pack is ready to be inserted into the pill intake reminder device 700, the system detects the pill pack 500 and uses the RFID reader 801 to read the value of the pill pack RFID tag 511. At this point, the system queries a database for the associated pill pack information to determine whether the pill pack 500 is associated with the patient for whom it is intended, i.e., the patient who will be using the pill intake reminder device 700. Once the verification is successful, i.e., a confirmation is received that determines that the right pills for the right patient are being inserted, an approval is provided to allow insertion of the pill pack 500 into the pill intake reminder device 700. If the system verification is unsuccessful, then the system prevents the insertion of the pill pack 500 into the pill intake reminder device 700.

The Wifi/SIM connectivity circuit 803 allows communications wirelessly and storage of data in its associated SIM memory chip. This can be used to record the retrieved RFID tags or store them for use as needed. The circuit also allows connections with RFID mechanisms.

The pill intake reminder device 700 also includes a battery pack 807. The battery pack 807 is located in the bottom housing 703. The battery pack 807 is used for storing charge and supplying power to the pill intake reminder device 700. Yet another method of powering the pill intake reminder device 700 includes DC current where the pill intake reminder device 700 can be plugged into a DC power outlet.

In one embodiment, a combination of both DC power and battery power may also be used. In this embodiment, the pill intake reminder device 700 may switch between the DC power and the battery power based on the availability of both, usually giving priority to DC power first and storing and recharging the battery pack 807 when the pill intake reminder device 700 is connected to DC power.

Figures 9A, 9B:
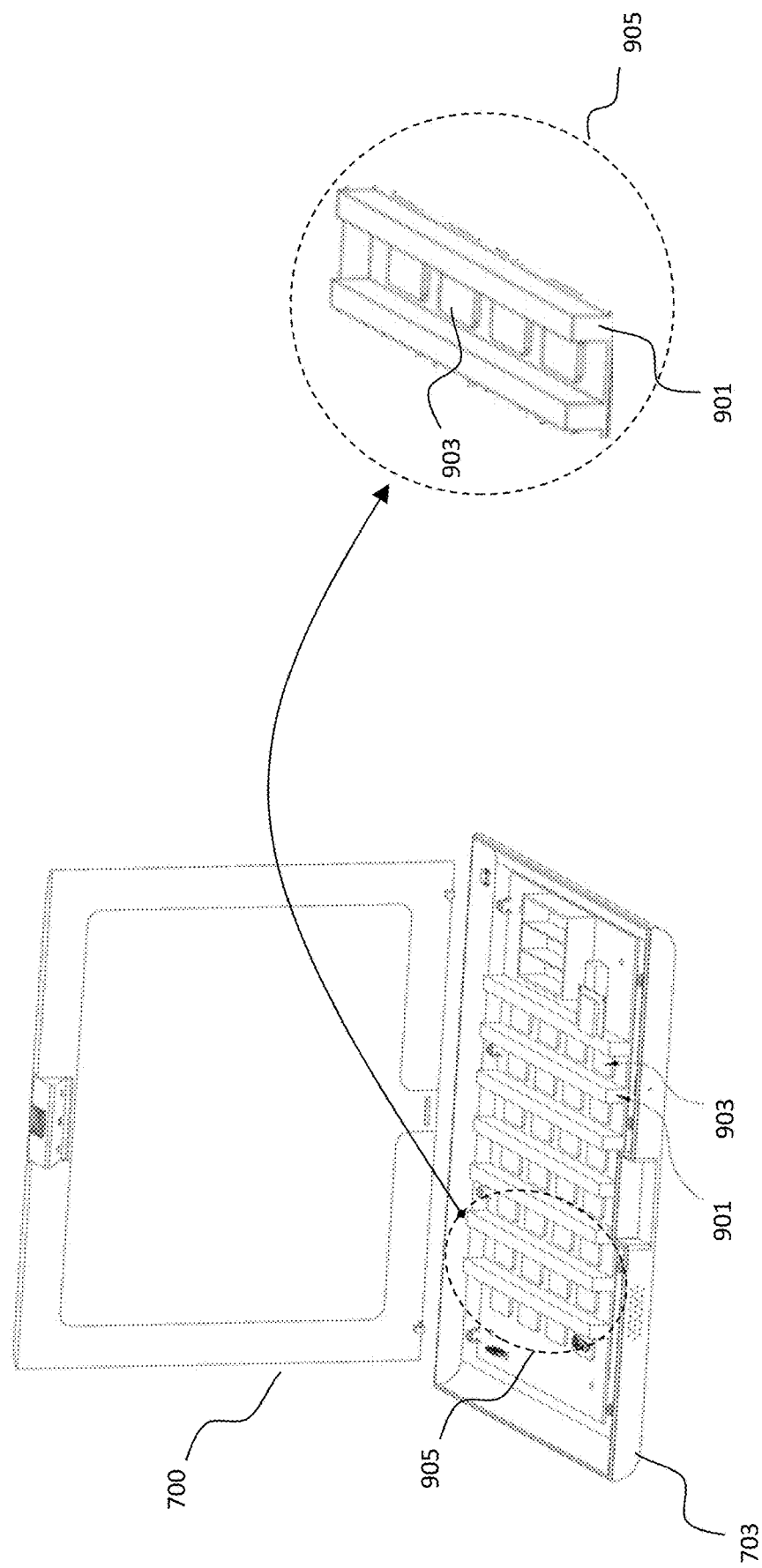
FIG. 9A depicts the pill intake reminder device including a plurality of IR sensors and cameras used by the pill intake reminder device according to the disclosed embodiments.
FIG. 9B is a detailed view of a row of plurality of IR sensors and cameras used by the pill intake reminder device according to the disclosed embodiments.

FIG. 9A depicts the pill intake reminder device including a plurality of IR sensors and cameras used by the pill intake reminder device according to the disclosed embodiments.

The pill intake reminder device 700 includes a plurality of Infrared (IR) Sensors and a plurality of cameras. The plurality of Infrared (IR) Sensors 901 are located in the bars 901. In operation, the mechanism that operates the IR Sensors 901 comprises a photodiode and a light emitting mechanism, such as in infrared light emitting diode (LED). In operation, a light beam, or an array of light beams, are passed from one bar to the next bar and through the transparent pouch of the pill pack 500. The light that passes through is read by the IR sensors and used for determining whether the pouch includes pills. For example, if the amount of light emitted is greater than the amount of light received at the other end, accommodating for some minimal light loss or diffraction, then the system detects an obstruction, the obstruction is due to the pills inside the pouch, and concludes that the transparent pouch includes pills inside it.

Once it is determined that the pouch contains pills, then a second determination is made as to the quantity of pills included in that pouch. A light passing through in its entirety from one bar to the next bar signifies that there was no obstruction of light, which implies that the transparent pouch did not contain any pills that would have blocked the light from passing through. An obstructed light signifies that there was some solid material that blocked the light from passing through and the amount of obstruction is measured to determine the number of pills remaining in the pouch. A small amount of light may be dispersed due to diffraction and that can be accounted for by the pill intake reminder device as tolerance for what amount of diffraction is allowed in still concluding that majority of the light passed through and as such there were no pills in that particular pouch. Further detail is provided below.

In one embodiment, the pill intake reminder device 700 contains eight bars 901. Since a pill pack contains seven rows and four columns, where seven rows correspond to seven days of the week from Monday to Sunday, when the pill pack 500 is inserted into the bottom housing 703, each column of the pill pack is placed in-between two bars 901 containing the photo diode and light emitting mechanism. This allows each column of the pill pack 500 to have light passed from one bar to another through its transparent pouch such that the passed light can be read to determine the number of pills in each pouch.

FIG. 9B is a detailed view of a row of plurality of IR sensors and cameras used by the pill intake reminder device according to the disclosed embodiments. As it can be seen, each row includes four cameras. When a pill pack in inserted in the bottom housing 703, each column of the pill pack, e.g. such as the column shown in FIG. 5 from pouches 504 (1)-504(4), is inserted between the two bars 901. Each column of the pill pack 500 contains four pouches, e.g., 504 (1)-504(4). The pouches 504 (1)-504(4) sit above the cameras 903 such that there is one camera underneath each pouch 504 (1)-504(4) of the pill pack. Further detail is described in FIGS. 10A and 10B.

Although eight bars 901 and four pouches 903 are depicted, other numbers and configurations are also contemplated. It is preferred to have at least one camera for each pouch and enough bars to allow each column of the pouch to sit in-between two bars, however, the configuration can be changed to accommodate for other pill packs of different configurations and number of pouches. Further, a single camera may also be used for monitoring multiple pouches.

FIG. 10A is a block diagram of a column of pouches of a pill pack and a column of IR sensors and cameras used by the pill intake reminder device according to the disclosed embodiments.

FIG. 10A shows a column of cameras and IR sensors mechanisms that is located in the bottom housing of the pill intake reminder device 700 of FIGS. 7, 8, and 9A. In this embodiment, a pill pack 500 is placed in the bottom housing 703 such that a column of the pill pack 500 enters the holes of the lower packing plate 709 (shown in FIG. 7) and sits in-between the two bars 1001 and 1003.

The column of pill pack 500 includes four transparent pouches 504(1)-504(4). Each pouch is placed above a camera. For example, pouch 504(1) sits above camera 1005, pouch 504(2) sits above camera 1007, pouch 504(3) sits above camera 1009, and pouch 504(4) sits above camera 1011. As such, each pouch 504(1)-504(4) is in-between bars 1001 and 1003 and overlays a camera.

The bar 1001 includes a plurality of IR sensors which have the capability to detect and measure light. The bar 1003 includes a plurality of light emitting diodes (LEDs). Each LED in bar 1003 is matched with an IR sensor in bar 1001. For example, LED 1015*a* is matched and aligned with IR sensor 1015*b*, LED 1017*a* is matched and aligned with IR sensor 1017*b*, LED 1019*a* is matched and aligned with IR sensor 1019*b*, and LED 1021*a* is matched and aligned with IR sensor 1021*b*.

Each pouch of the pill pack includes an LED on one side and an IR sensor on the other side. For example, pouch 504 (1) is placed in-between an LED 1015*a* that is located in bar 1003 and an IR sensor 1015*b* that is placed in bar 1001. Since the pouch is transparent, light emitted from the LED passes through the transparent pouch and reaches the IR sensor. The light is then detected and measured by the IR sensor to determine whether all or some of the light emitted from the Led reached the IR sensor.

In on embodiment, all the pouches 504(1)-504(4) included 3 pills that were designated for a specific the patient, i.e., user of the pill intake reminder device 700. The pills in pouch 504(1) were to be taken by the patient in the morning, pills in pouch 504(2) were to be taken by the patient in the afternoon, pills in pouch 504(3) were to be taken by the patient in the evening, and pills in pouch 504(4) were to be taken by the patient at night.

After each hour of administration, i.e., morning, afternoon, evening, and night, the pill intake reminder device 700 runs a scan of the pouches in the pill pack to determine whether the patient took all the pills that were intended to be taken for that hour of administration. In this instance, looks like pouch 504(1) currently has 3 pills, pouch 504(2) currently has no pills, pouch 504(3) currently has 2 pills, and pouch 504(4) currently has no pills.

In one embodiment, the pill intake reminder device 700 with its IR sensors and LED performs the scan on the pouches 504(1)-504(4) in the following manner. LED 1019*a* emits light that is to be passed through pouch 504 (3) and received at IR sensor 1019*b*. Detailed FIG. 10B will be used to explain how the pill intake reminder device 700 uses the IR sensors and LED to determine the number of pills in the pouch.

FIG. 10B is a detailed view of a single pill pack's pouch and IR sensors and cameras used to detect pills in the pouch by the pill intake reminder device according to the disclosed embodiments.

An IR sensor 1019*b* and an LED 1019*a* is used in this embodiment. The IR Sensor 1019*b* uses a specific light sensor to detect a select light wavelength in the IR spectrum. The LED 1019*a* emits a light at a certain wavelength. This light is invisible to our eyes and it can be detected by an infrared sensor. Typically, the light emission by the LED is at the same wavelength as what the sensor 1019*b* is looking for, such that the IR sensor can read the intensity of the received light. The LED or the emitter is simply an IR LED and the detector is simply an IR photodiode. When a pill, such as pills 1023 and 1025 are in the path or line of sight between the light that is emitted from the LED and to be received IR sensor, the light from the LED bounces off the object reflects back. If the light passes through without obstruction, it is received by the IR sensor 1019*b* and results in a large jump in the intensity, which can be detected using a threshold.

As it can be seen in FIG. 10*b*, there are two pills 1023 and 1025. To illustrate this point, let us imagine that three pills were deposited in all the pouches 504(1)-504(4) in the pill pack in FIG. 10*a*.

In FIG. 10*b*, first a camera 1009 that is placed underneath the transparent pouch 504 (3) detects that there is some object in the pouch and alerts the pill intake reminder device 700 to run a scan on the pouch 504 (3). The pill intake reminder device 700 then using LED 1019*a* allows a light to be emitted in the direction of the IR sensor 1019*b*. The line of sight of the light is obstructed by the two pills 1023 and 1025, however, some light whose line of sight with the IR sensor is above the pills 1023 and 1025 escapes and reaches the IR sensor. The IR sensors 1019*b* measures the intensity of light and the line of sight to determine whether it was obstructed. Since the pills 1023 and 1025 obstruct some portion of the light, the pill intake reminder device 700 analysis the reading and comes to a conclusion that some pills in the pouch remain. An area of missing light is also used in the determination, e.g., light in a rectangular or oval section in the bottom right side has been obstructed. The pill intake reminder device 700 may either confirm the number of pills or use the camera as a secondary check to image and determine the number of pills that remain in the pouch.

Alternatively, the same routine may be executed in a different sequence. For example, first a scan may be performed using the IR sensor and the LED to determine whether any obstruction is detected. If an obstruction is detected, then the camera may be used to image and determine the exact number of pills that remain in the pouch. The IR sensors and LED along with the camera may be used in other combination to determine the presence of a pill and then do an exact count. In the present case, the combination will determine that two pills remain. The pill intake reminder device 700 may then sound an alarm or produce an alert. The alarm or alert will be to inform the patient that the pills that were required to be taken evening are not taken, either partially or in full. The pill intake reminder device 700 may be set up to alert the caregiver or family/friends through SMS messaging, email, or sound an alarm on their mobile phone depending on the parameters that were used to set the system and alert preferences.

Referring back to FIG. 10*a*, pouch 504 (1), which holds pills for morning hour of administration, the pill intake reminder device 700 uses LED 1015*a* to emit a light that will be received by IR sensor 1015*b*. The light emitted is completely obstructed by the pills and not received by the IR sensor 1015*b*. As such pill intake reminder device 700 determines that none of the pills are taken and sounds an alarm and/or alert as either customized by the user or the caregiver or automated by pill intake reminder device 700. A camera 1005 may be used to further confirm the findings of the IR sensor and LED mechanism.

With respect to pouch 504 (2), which holds pills for afternoon hour of administration, the pill intake reminder device 700 uses LED 1017*a* to emit a light that will be received by IR sensor 1017*b*. The light emitted received in its entirety by the IR sensor 1017*b*. As such pill intake reminder device 700 determines that all the pills were taken by the user. Since all the pills were taken, the camera 1007 does not need to be used to verify or count the pills in the pouch.

Likewise, pouch 504 (4), which holds pills for night hour of administration, the pill intake reminder device 700 uses LED 1021*a* to emit a light that will be received by IR sensor 1021*b*. The light emitted received in its entirety by the IR sensor 1021*b*. As such pill intake reminder device 700 determines that all the pills were taken by the user. Since all the pills were taken, the camera 1011 does not need to be used to verify or count the pills in the pouch.

Figure 11:
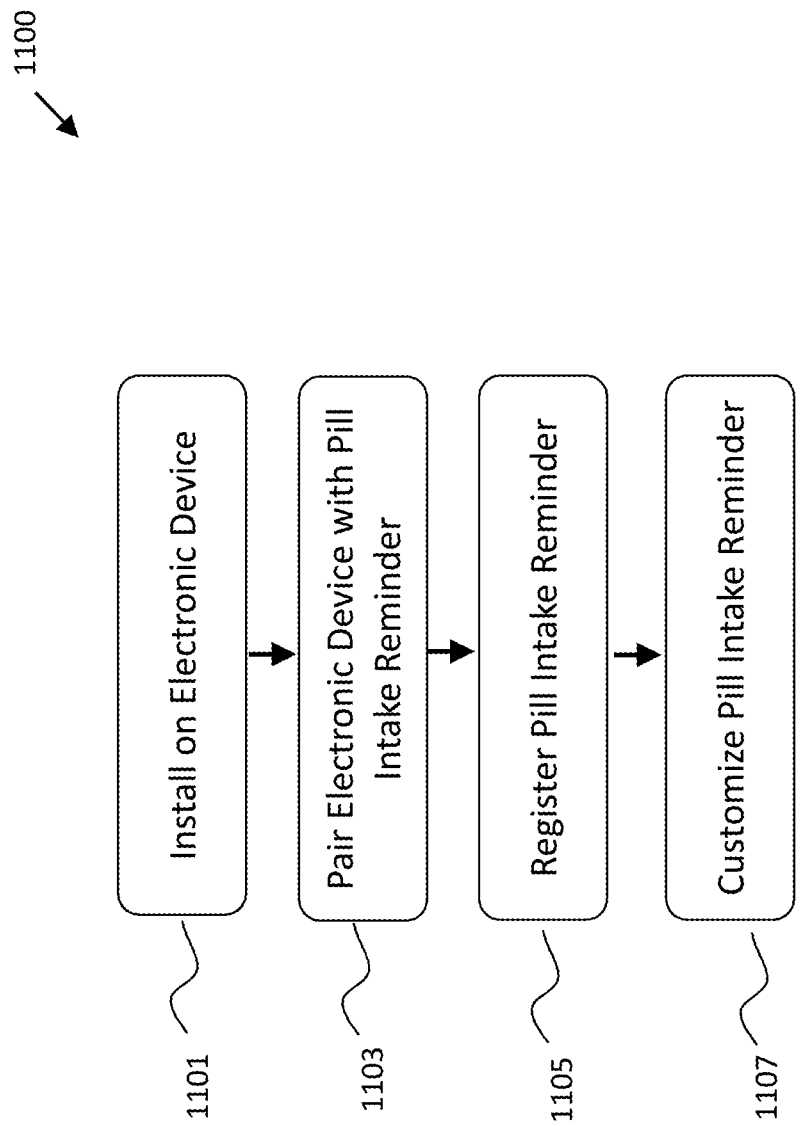
FIG. 11 is a flow chart for installing and registering the pill intake reminder device according to the disclosed embodiments.

FIG. 11 is a flow chart for installing and registering the pill intake reminder device according to the disclosed embodiments. The steps depicted in flow chart 1100 are interchangeable and may include additional steps in-between.

Step 1101 provides details of installing a mobile application on a mobile phone or tablet or smart watch to connect an operate the pill intake reminder device 700. At step 1101, a user searches their APP Store on their mobile device or tablet to find an Application for the pill intake reminder device. The user then downloads the Application on their electronic device that is capable or communicating with the Internet.

At Step 1103, the pill intake reminder device is paired with the electronic device. Standard pairing methods through Bluetooth, WIFI and others are used to pair the two devices. A password and User ID may also be required to complete the pairing of the two (or more) devices. The method may also involve, connecting to the local WIFI and restarting and rebooting one or both devices.

At Step 1105, the pill intake reminder device is registered. This may involve the user to create a profile, login credentials, allow the system to read the user's fingerprints through the fingerprint reader, contact details for the caregiver, family, friends all of whom the user wishes to inform and share the data. The registration may also include inputting voice recordings through an IVR by calling or through the microphone of the pill intake reminder device.

The registered data is stored in the memory of the pill intake reminder device as part of the user identification and interaction module as shown in FIG. 2. The registered data is used by the pill intake reminder device to confirm the identity of the user and caregiver that is authorized and provide the right level of access to the device and the data stored by the pill intake reminder device.

At Step 1107, the pill intake reminder device is customized by the user. Customization may include types of alerts, colors of lights used for alerts, types and intensity of audible alarms, types of notifications to caregivers on the authorized alert list, frequency of the alarms and other options mentioned above. Alternatively, the user may choose to the standard automated settings of the pill intake reminder device.

Once registration and customizations are completed, the pill intake reminder device is ready for use.

Figure 12:
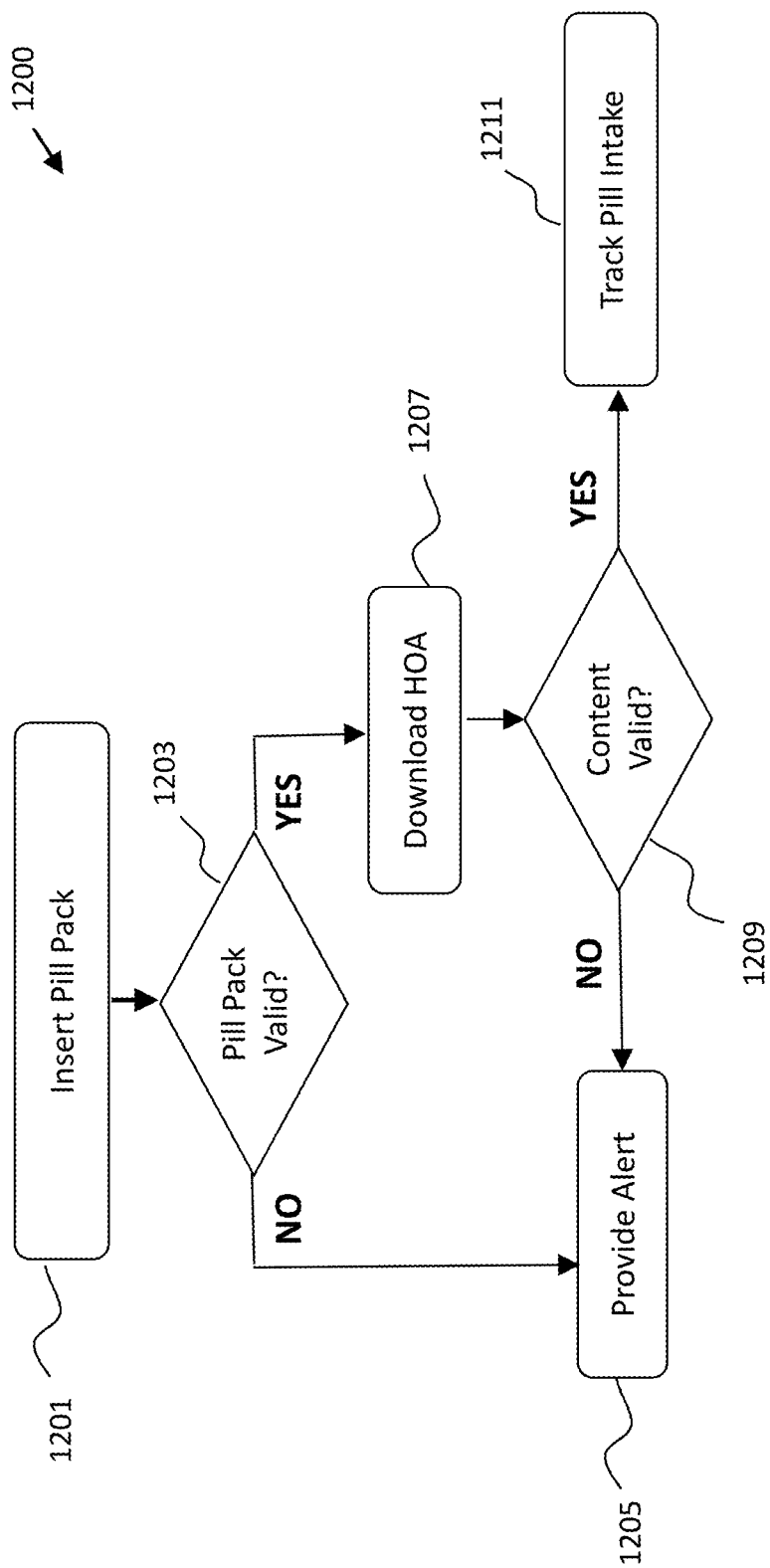
FIG. 12 is a flow chart for inserting and verifying a pill pack that is to be used by the pill intake reminder device according to the disclosed embodiments.

FIG. 12 is a flow chart for inserting and verifying a pill pack that is to be used by the pill intake reminder device according to the disclosed embodiments. The pill pack 500 is depicted in FIGS. 5 and 6 above and the insertion of the pill pack is in-between the upper and the lower packing plate as described in FIG. 7 and the related description above.

At Step 1201, a pill pack 500 is inserted in-between the upper and the lower packing plate of the pill intake reminder device 700. The pill pack includes a plurality of pills that are to be taken by the user at different hours of administration (HOA). The pill pack may be delivered to the user by a pharmacy, doctor, or caregiver. The pill pack include an RFID tag that holds information specific to the patient.

Upon insertion, the pill intake reminder device 700 reads the RFID tag of the pill pack 500 using an RFID reader. The patient data is then sent to a database and queried for verification. The process matching the patient data from the RFID with the database to ensure that a correct pill pack, one that is associated with the patient for whom it is intended, i.e., the patient who will be using the pill intake reminder device 700 is being inserted. As such, information such as Patient Name and prescription may be matched.

If verification is unsuccessful, i.e., patient data is not matched through the database, then at Step 1205, the pill intake reminder device 700 provides an alert. This alert may be audible, SMS, display of a certain light, such as a red light that will inform the user of the wrong pill pack. The alerts can be customized at the time of registration and customization step as described in FIG. 11. The alert may also be to inform the pharmacy, or the person or institution that provided the pill pack, that a wrong pill pack was provided by them and that a new and correct pill pack (or replacement pill pack) associated with the specific user is requested.

If verification is successful, i.e., a confirmation is received that determines that the right pills for the right patient are being inserted, then at Step 1207 an approval is provided to allow insertion of the pill pack 500 into the pill intake reminder device 700.

Upon a successful verification, at Step 1207, the pill intake reminder device 700 downloads all the hours of administration (HOA) for the pills inside the pill pack 500. This includes the times when each pill in each pouch is to be taken by the user. The pill intake reminder device 700 may download the HOAs from the cloud and store them into memory.

At Step 1209, a second verification is performed to ensure that correct pills are being held in each pouch of the pill pack 500 that is inserted in the pill intake reminder device 700. For example, such a verification confirms at a detailed level that a particular pouch, say the pouch for Wednesday Morning which was suppose to contain 4 pills in fact does contain four pills and no more or no less. This verification is performed using the IR sensor and Camera as described in FIGS. 9A, 9B, 10A, and 10B.

The verification includes emitting a light using an LED through each transparent pouch which holds pills for the user. The emitted light is then received by IR sensor and measured. The light emitted is either partially blocked, received in its entirety or completely blocked. Aside from minor distortions of light, the IR sensors measures the light received to determine if there are any contents in the pouch. If there is any inconsistency from the HOA downloaded, such as a particular pouch needs to have some pills and there are no obstructions of light signifying that there are no contents in that pouch, then the pill intake reminder device 700 provides an alert at Step 1205. Likewise, if there is a mismatch of reading, such as there should be no pills in a particular pouch of the pill pack 500 and the IR sensor and LED mechanism detect that there are some contents, then there is an error and the pill intake reminder device 700 provides an alert.

The verification also includes use of a camera that is located underneath each pouch. The camera analyses the contents of each pouch and reports it to the pill intake reminder device 700. The camera and the IR sensor-LED mechanism work together to determine the contents of each pouch, which includes type and quantity of pills in each pouch.

At Step 1211, the pill intake reminder device 700 tracks the intake of the pills in it pouches. It does so by scanning each pouch at the time of its HOA and determines whether all the pills from that pouch have been emptied by the user at the HOA. If they have not, then the pill intake reminder device 700 sends an alert to the user, caregiver, and others in the list of priority of notification set by the user or their caregiver. It may also perform a periodic or scheduled scan on a routine or custom timed basis to check on the status of the pill intake.

Figure 13:
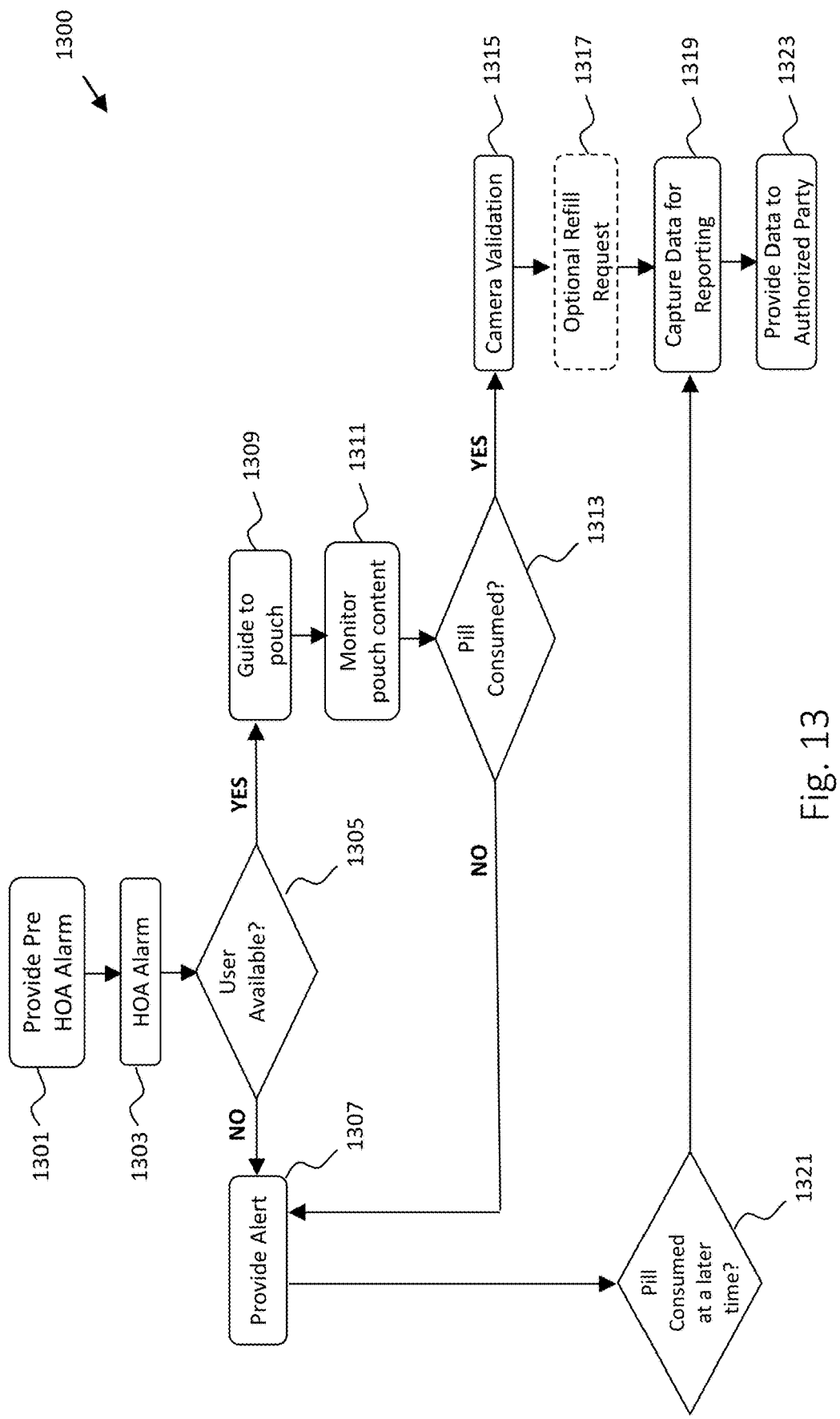
FIG. 13 is a flow chart of one cycle of operation of the pill intake reminder device according to the disclosed embodiments.

FIG. 13 is a flow chart of one cycle of operation of the pill intake reminder device according to the disclosed embodiments.

At Step 1301, the pill intake reminder device 700 sounds or displays an alarm. This alarm can be audible, visual, or both. The alarm can either be in accordance with a standard pill intake reminder device 700 setting, such as 10 minutes before the HOA or it can be customized by the user or caregiver to be set off at a predetermined time, such as 5, 10, 15, or 20 minutes or some other number. The user can also choose to have multiple alarms or alarms that sounds and are visually displayed differently based on the amount of time before the HOA. For example, the user can have an audible alarm set for 15 minutes before HOA, 10 minutes before HOA, and 5 minutes before HOA eacj increasing in volume as it gets closer to the HOA. The user can also have different light displays as it gets closer to time.

At Step 1303, a second alarm can be set at the exact time of HOA. This alarm, along with the alarm mentioned in step 1301 can also vibrate the pill intake reminder device 700 or vibrate, sound, and display an electronic device, such as a mobile phone, tablet, that is paired with the pill intake reminder device 700.

Alternatively, the user may choose to have only one alarm at HOA and no alarm before the HOA or vice versa. They may also choose to have no alarm at all before or at the time of HOA.

At Step 1305, the pill intake reminder device 700 checks to see if the user has interacted with the device. Since the alarm has already sounded, or in the event the user doesn't not have an alarm before the HOA, the pill intake reminder device 700 waits for the user to open the device or unlock the device. If the user does not interact with the device, then at Step 1307, the pill intake reminder device 700 provides another alert. This alert can be different from the alerts set for pre HOA or HOA alarm.

When the user does interact with the pill intake reminder device 700, a previously set audible greeting may be sounded through the speaker of the pill intake reminder device 700. There may also be an audible message that goes along with the pills the user is to take at the HOA. For example, an instruction to take it after food may be sounded at the time of HOA to remind the user that they need to consume some food before taking the pills.

At Step 1307, if the user does interact with the pill intake reminder device 700, then the system determines that the user is available to take the pills. As such, the pill intake reminder device 700 at Step 1309 lights up the area surrounding the pouch of the pill pack in which the pills for the HOA are deposited. This guidance visually aids the user to pick the pills out of the correct pouch of the pill pack and consume them. The visual guidance also makes it easy and convenient so the users don't have to read the details, them may not be fully alert and can still take the correct medications.

At Step 1311, the pill intake reminder device 700 performs a scan of the pouch in which the pills for the HOA were housed. The scan is a secondary check to determine if the pills from the pouch, the pouch which was previously lighted by the pill intake reminder device 700 for guiding the user, were removed from the pouch. The pill intake reminder device 700 determines if all or some of the pills were removed. It does so by using the IR sensor and LED light mechanism in conjunction with the camera. As described in greater detail in FIGS. 9A, 9B, 10A, and 10B and the related text above. In brief, the LED emits light in the direction of the IR sensor. The emitting is passed through the transparent pouch which holds pills for the user. The emitted light is then received by IR sensor and measured. The measurement determines whether any pills remain in the pouch thereby confirming that the user has not taken all the pills at the intended HOA. The camera confirms the check performed by the IR sensor and the led mechanism through actual images.

At Step 1313, if a determination is made that the user has not consumed all the pills in the pouch, then the pill intake reminder device 700 provides an alert 1307.

At step 1315, the pill intake reminder device 700 performs a camera validation to confirm that no pills remain in the pouch that were to be consumed.

Optionally, at Step 1317, the user can send a message to the pharmacy by using the pill intake reminder device 700 to request a refill. This may be applicable to certain patients that routinely take the same medication or have a prescription that allows for refills.

At step 1319, the data is captured for reporting. The data may be that the user consumed all the pills in the pouch. The data may also include the times of intake, late intake, number of alarms sounded, and partial intake.

At step 1321, for any pills that were not consumed at the HOA, either at step 1305 or at step 1313 due to which an alert 1307 was provided, the pill intake reminder device 700 checks to see if the user took the pills out of the pouch at a later time. If the user did not consume it at a later time, then non-compliance is recorded at Step 1319.

At step 1323, the captured data is available for the doctor, caregiver, or any authorized person who is allowed to obtain the patient data.

The alerts at Step 1307 can also be provided to authorized caretakers at the time of non-compliance. For example, if a user misses the HOA, then the caregiver's mobile phone, smart watch, tablet, and/or any device previously authorized will receive at audible, visual, or vibrating alert. The caregiver may then either call the user or send a voice message or speak live through the pill intake reminder device 700's speaker to the user to remind them to take the medication.

It will be apparent to those skilled in the art that various modifications and variations can be made in the disclosed embodiments of the disclosed device and associated methods without departing from the spirit or scope of the invention. Thus, it is intended that the present invention covers the modifications and variations of the embodiments disclosed above provided that the modifications and variations come within the scope of any claims and their equivalents.

What is claimed is:

1. A computerized pill intake reminder device for detecting pills that have been stored inside the pouches of the device and for reminding its users to take their pills at their hours of administration, comprising:
    a top housing having an interior side and an exterior side;
    a bottom having an interior side and an exterior side, the bottom housing coupled to the top housing such that the top housing can be rotated about the bottom housing to form a closed module or be rotated to form an open module, wherein the closed module results in the interior side of the top housing facing the interior side of the bottom housing and closed and both interiors closed to the outside;
    a processor housed within the bottom housing, wherein the processor is communicatively coupled through an electronic circuit to a plurality of electronic components housed within the pill intake reminder device;
    a speaker housed within the bottom housing, wherein the processor causes the speaker to sound an audible alarm or an audible message at a specific time thereby reminding the user of the pill intake reminder device to retrieve a pill housed within and consume that pill at its hour of administration;
    a pill storage module housed within the bottom housing, wherein the pill storage module includes an upper packing plate and a lower packing plate and space in-between the upper and lower packing place to removably receive a pill/blister pack having a plurality of pill storage pouches for storing pills;
    a pill detection module housed within the bottom housing, wherein the pill detection module includes an infrared sensor and a camera, wherein the processor causes the infrared sensor to detect the presence of a pill inside the pouch of the pill/blister pack and the processor causes the camera to quantify the number of pills in the pouch; and
    a guidance system coupled to the upper packing plate of the pill storage module, wherein the processor causes the guidance system to guide the user of the pill intake reminder device to a specific pouch of the pill/blister pack for retrieving pills stored in that pouch.

2. The computerized pill intake reminder device of claim 1, further comprising a fingerprint scanner, wherein the fingerprint scanner is housed within the bottom housing of the pill intake reminder device, wherein the fingerprint scanner is used for providing authorized access for depositing or retrieving pills from the pill intake reminder device.

3. The computerized pill intake reminder device of claim 1, further comprising a display, wherein the processor causes the display to depict messages, images, or videos relating to the pill stored within the pill intake reminder device.

4. The computerized pill intake reminder device of claim 1, wherein the guidance system includes a light emitting diode (LED), wherein the upper packing plate includes a plurality of cut outs or holes, the placement of the holes is such that each hole overlays a pouch of the pill/blister pack, wherein the LED lights up a specific hole of the upper packing plate that overlays a specific pouch from which pills are to be retrieved by the user for consumption.

5. The computerized pill intake reminder device of claim 1, further comprising an alert system, wherein the alert system utilizes the processor thereby causing the speaker to sound the audible alarm or an audible pre-recorded message, wherein the alert system further comprises communicating an alert to one or more mobile devices that are authorized to receive an alert from the alert system.

6. The computerized pill intake reminder device of claim 1, further comprising a radio frequency identification (RFID) reader, wherein the processor causes the RFID reader to scan a RFID tag that is located on the pill/blister pack, wherein the insertion of the pill/blister pack into the pill storage module is allowed after confirmation of the RFID tag.

7. The computerized pill intake reminder device of claim 1, further comprising a microphone for recording messages that can be stored in the pill intake reminder device.

8. The computerized pill intake reminder device of claim 1, further comprising a transmitter and a receiver, wherein the transmitter is used to send data to an external device and a receiver is used for receiving data from an external device.

9. A computerized method for managing pill intake compliance and associated reminders to a user, wherein the pills are housed in an electronic module that is communicatively connected to a plurality of electronic devices, the method comprising:
using a foldable electronic module having a top housing and a bottom housing, wherein the bottom housing is coupled to the top housing such that the top housing can be rotated about the bottom housing to form a closed and sealed module or be rotated to form an open module, wherein the electronic module can go from the closed and sealed to open module position or vice versa either manually or though voice activation, wherein the foldable electronic module includes a plurality of electronic components, wherein the foldable electronic module includes a memory for storing and retrieving data, wherein the bottom housing includes a pill storage module that includes an upper packing plate and a lower packing plate and space in-between the upper and lower packing place to removably receive a pill/blister pack having a plurality of pill storage pouches for storing pills;
using a processor that is housed within the bottom housing, wherein the processor is communicatively coupled through an electronic circuit to a plurality of electronic components housed within the foldable electronic module;
receiving a pill/blister pack to house in-between the upper and lower packing plate of the bottom housing, wherein the pill/blister pack has one or more pills stored within its pouch;
using a display, which is one of the electronic components communicatively coupled to the processor, wherein the processor causes the display to depict an instruction or a video that relates to the intake of a pill stored within a pill pouch;
alerting the user of the foldable electronic module to retrieve a pill from the foldable electronic module and consume the pill;
guiding the user of the foldable electronic module by illuminating a light emitting diode (LED) on a specific pouch of the pill/blister pack thereby guiding the user to retrieve the pills inside the specific pouch; and
in the event pills are not retrieved after the alerts is provided, transmitting a second alert to the user or a designated recipient thereby informing them of the noncompliance that the user has not retrieved the pill within an allotted amount of time from the proving of the first alert.

10. The method of claim 9, further comprising:
determining if one or more pills are stored in a pouch of the pill/blister pack, wherein the determining is performed using an infrared sensor, the determining comprising
using a light emitting source to project light such that the light passes through a pouch of the pill/blister pack,
using an Infrared Sensor to receive the light emitted by the light emitting source,
calculating the amount of light emitted and the amount of light received to determine if some or all of the light was obstructed,
upon a determination that at least some of the light was obstructed, using a processor to activate a camera that is positioned underneath the pouch of the pill/blister pack, imaging the pouch, and performing a count of the pills remaining in the pouch, and
reporting the results of the amount of light obstructed.

11. The method of claim 10, wherein the second alert is sent if a determination is made that the pouch contains pills that were to be retrieved by the user.

12. The method of claim 9, wherein the second alert is sent to a mobile device of a recipient that is authorized to received such alerts.

13. The method of claim 9, wherein alerting the user of the foldable electronic module is performed by the processor causing the activation of an alarm such that the alarm produces an audible sound.

14. The method of claim 9, further comprising a periodic pill/blister pack inventory verification system, wherein the periodic verification includes scanning each pouch of the pill/blister pack using an Infrared Sensor and imaging each pouch with a camera.

15. The method of claim 9, wherein alerting the user of the foldable electronic module is performed by illuminating a light emitted diode (LED) which is the located on the exterior of the foldable electronic module.

16. The method of claim 12, further comprising using a transmitter that is housed inside the foldable electronic module to send an alert if a determination is made that a particular pouch contains one or more pills that exceeds the number of pills that are required to be in that pouch at a specific time.

17. The method of claim 15, wherein guiding the user of the foldable electronic module by illuminating a light emitting diode (LED) further comprises:
obtaining the hours of administration (HOA) schedule;
locating a pouch of the pill/blister pack that correlates with the HOA schedule, wherein such correlation implies that the specific pouch holds medical pills that are to be taken at that specific time in accordance with the HOA schedule; and electronic module;
illuminating the pouch by using an LED.

18. A computerized method for managing pill inventory in a blister pack housed in an electronic module comprising:
- using an electronic module that has a top housing and a bottom housing, wherein the top housing can be rotated about the bottom housing to form a closed electronic module or be rotated to form an open module, wherein the electronic module includes a processor, nonvolatile memory, a plurality of infrared sensors, and a plurality of cameras, wherein the electronic module include a section for receiving and storing a blister pack, wherein the electronic module includes a radio frequency (RFID) scanner;
- verifying the blister pack that is to be inserted in the electronic module, wherein the blister pack includes medical pills designated for a specific user/patient, wherein verification includes the processor activating the RFIID scanner to scan a RFID tag located on the blister pack and match the data from the RFID tag with the data stored in the nonvolatile memory to ensure that the blister pack matches with the user that is to consume the pills housed in the blister pack;
- the processor unlocking the section in which the blister pack is to be housed once a positive match is made;
- providing an alert informing the user/patient that it is time to take their medical pills;
- illuminating a pouch of the blister pack that houses the medical pills that are to be taken at the time of the alert;
- electronically determining if the patient retrieved the pills from the pouch within a certain preprogrammed window of time, wherein the electronic determination further comprises performing an error detection analysis to determine if the required number of pills were retrieved from the pouch of the blister pack, wherein the error detection includes using an infrared sensor housed within the electronic module to determine the presence of one or more pills in the pouch and using a camera housed underneath the pouch to image and count the number of pills that are in the pouch; and
- providing an alert to the user or an authorized caregiver is the pills were not retrieved within the preprogrammed window of time.

19. The method of claim 18, wherein the alert to the user or an authorized caregiver is sent to a mobile phone.

* * * * *